US010398233B2

(12) United States Patent
Hoyt et al.

(10) Patent No.: US 10,398,233 B2
(45) Date of Patent: Sep. 3, 2019

(54) SYSTEM ARCHITECTURE FOR OFFICE PRODUCTIVITY STRUCTURE COMMUNICATIONS

(71) Applicant: Herman Miller, Inc., Zeeland, MI (US)

(72) Inventors: Christopher Hoyt, Grand Rapids, MI (US); Daniel Rucker, Grand Rapids, MI (US); Joseph Doran, Round Rock, TX (US); Brian Alexander, Douglas, MI (US); Adam Daley-Fell, Zeeland, MI (US)

(73) Assignee: HERMAN MILLER, INC., Zeeland, MI (US)

( * ) Notice: Subject to any disclaimer, the term of this patent is extended or adjusted under 35 U.S.C. 154(b) by 230 days.

(21) Appl. No.: 14/982,758

(22) Filed: Dec. 29, 2015

(65) Prior Publication Data

US 2016/0183687 A1    Jun. 30, 2016

Related U.S. Application Data

(60) Provisional application No. 62/097,439, filed on Dec. 29, 2014, provisional application No. 62/174,333, filed on Jun. 11, 2015.

(51) Int. Cl.
*A47C 1/03* (2006.01)
*A47C 7/56* (2006.01)
(Continued)

(52) U.S. Cl.
CPC ............... *A47C 7/62* (2013.01); *A47C 1/03* (2013.01); *A47C 7/56* (2013.01); *A47C 31/126* (2013.01);
(Continued)

(58) Field of Classification Search
CPC .......... A47C 31/126; A47C 7/56; G05B 15/02
See application file for complete search history.

(56) References Cited

U.S. PATENT DOCUMENTS

| 6,964,370 B1 | 11/2005 | Hagale et al. |
| 8,714,645 B2 | 5/2014 | Cvek |

(Continued)

FOREIGN PATENT DOCUMENTS

| CN | 102058264 A | 5/2011 |
| CN | 103504843 A | 1/2014 |

(Continued)

OTHER PUBLICATIONS

Translation of KR10-2014-0032082 (original document provided in IDS filed on Aug. 16, 2016).*

(Continued)

*Primary Examiner* — Changhyun Yi
(74) *Attorney, Agent, or Firm* — Michael Best & Friedrich LLP

(57) ABSTRACT

A furniture system includes a chair having a seat, a backrest coupled to the seat, and a base supporting the backrest and the seat. The furniture system also includes a plurality of sensors and a processor. Each sensor is operable to detect a physical force imparted by a user on the chair, and generate an output signal indicative of the physical force. The processor is coupled to the plurality of sensors, and is operable to receive the output signals generated by the plurality of sensors, and determine, based on at least one of the output signals, a current posture of the user sitting in the chair.

21 Claims, 19 Drawing Sheets

(51) Int. Cl.
  *A47C 7/62* (2006.01)
  *A61B 5/00* (2006.01)
  *A61B 5/11* (2006.01)
  *A47C 31/12* (2006.01)
  *A61B 5/103* (2006.01)

(52) U.S. Cl.
  CPC .......... *A61B 5/4561* (2013.01); *A61B 5/6891* (2013.01); *A61B 5/0022* (2013.01); *A61B 5/1036* (2013.01); *A61B 5/1116* (2013.01)

(56) References Cited

U.S. PATENT DOCUMENTS

| | | | |
|---|---|---|---|
| 8,714,646 B2 | 5/2014 | Cvek | |
| 8,947,215 B2 | 2/2015 | Mandel et al. | |
| 9,380,682 B2 | 6/2016 | Mead et al. | |
| 9,642,219 B2 | 5/2017 | Mead et al. | |
| 9,766,079 B1 | 9/2017 | Poel et al. | |
| 9,852,388 B1 | 12/2017 | Swieter et al. | |
| 9,921,726 B1 | 3/2018 | Sculley et al. | |
| 9,955,318 B1 | 4/2018 | Scheper et al. | |
| 10,021,530 B2 | 7/2018 | Sigal et al. | |
| 2004/0010328 A1 | 1/2004 | Carson et al. | |
| 2008/0155429 A1 | 6/2008 | Frank et al. | |
| 2009/0273441 A1 | 11/2009 | Mukherjee | |
| 2010/0198374 A1 | 8/2010 | Carson et al. | |
| 2010/0212087 A1 | 8/2010 | Leib et al. | |
| 2011/0275939 A1* | 11/2011 | Walsh ................. | A61B 5/4561 600/473 |
| 2011/0295392 A1 | 12/2011 | Cunnington et al. | |
| 2013/0113249 A1 | 5/2013 | Cvek | |
| 2013/0117158 A1 | 5/2013 | Cvek | |
| 2013/0199420 A1 | 8/2013 | Hjelm | |
| 2013/0204438 A1 | 8/2013 | Hjelm | |
| 2013/0275267 A1 | 10/2013 | Cvek | |
| 2014/0203919 A1 | 7/2014 | Baker et al. | |
| 2014/0203921 A1 | 7/2014 | Baker et al. | |
| 2014/0238169 A1 | 8/2014 | Cvek | |
| 2014/0239688 A1 | 8/2014 | Cvek | |
| 2014/0302795 A1 | 10/2014 | Chacon et al. | |
| 2014/0319892 A1 | 10/2014 | Boccara | |
| 2017/0208664 A1 | 7/2017 | Mead et al. | |

FOREIGN PATENT DOCUMENTS

| | | |
|---|---|---|
| CN | 104055353 A | 9/2014 |
| CN | 203943350 U | 11/2014 |
| EP | 1832202 A1 | 9/2007 |
| KR | 100876632 | 12/2008 |
| KR | 1020090058627 | 6/2009 |
| KR | 1020120132875 | 12/2012 |
| KR | 1020140011092 | 1/2014 |
| KR | 20140032082 A | 3/2014 |
| KR | 1020140032082 | 3/2014 |
| WO | 0215748 A1 | 2/2002 |
| WO | 03001946 A1 | 1/2003 |
| WO | 2015032545 | 3/2015 |

OTHER PUBLICATIONS

Translation of KR10-2014-0011092 (original document provided in IDS filed on Aug. 16, 2016).*
Search Report from the International Searching Authority for Application No. PCT/US2015/067861 dated Apr. 18, 2016 (6 pages).
Written Opinion from the International Searching Authority for Application No. PCT/US2015/067861 dated Apr. 18, 2016 (10 pages).
European Extended Search Report for related Application No. 15876167.6 dated Jun. 14, 2018 (7 pages).
First Office Action issued from the Chinese Patent Office for related Application No. 201580077042.8 dated May 7, 2019 (22 Pages including English Translation).

* cited by examiner

SYSTEM ARCHITECTURE FOR OFFICE PRODUCTIVITY STRUCTURE COMMUNICATIONS

CROSS-REFERENCE TO RELATED APPLICATIONS

This application claims priority benefit to U.S. Provisional Application No. 62/097,439 filed Dec. 29, 2014 and U.S. Provisional Application No. 62/174,333 filed Jun. 11, 2015, the entire contents of both of which are hereby incorporated by reference.

BACKGROUND

Every year executives and employees spend millions of hours seated while working. Productivity of executives and employees will ultimately affect the output, and consequently, the profitability of a company. Devices and/or other workplace structures designed to aid workers in determining optimal work habits and improving interaction with other workers may increase per capita output. Thus, improvements in how devices and systems facilitate habits and interactions may drive consumer demand for these products.

SUMMARY

In one embodiment, the invention provides a furniture system including a chair having a seat, a backrest coupled to the seat, and a base supporting the backrest and the seat. The furniture system also includes a plurality of sensors coupled to the chair. Each sensor is operable to detect a physical force imparted by a user on the chair, and generate an output signal indicative of the physical force. The furniture system further includes a processor coupled to the plurality of sensors. The processor is operable to receive the output signals generated by the plurality of sensors, and determine, based on at least one of the output signals, a current posture of the user sitting in the chair.

In another embodiment, the invention provides a method of determining a posture of a user sitting in a chair. The chair includes a seat, a backrest, and a base. The method includes detecting, by a plurality of sensors coupled to the chair, a physical force imparted by the user on the chair, and generating, by each of the plurality of sensors, an output signal indicative of the physical force. The method also includes receiving, by a processor coupled to the plurality of sensors, the output signals generated by the plurality of sensors, and determining, by the processor, a current posture of the user sitting in the chair based on at least of one of the output signals received by the processor.

Other aspects of the invention will become apparent by consideration of the detailed description and accompanying drawings.

DETAILED DESCRIPTION

Figure 1:
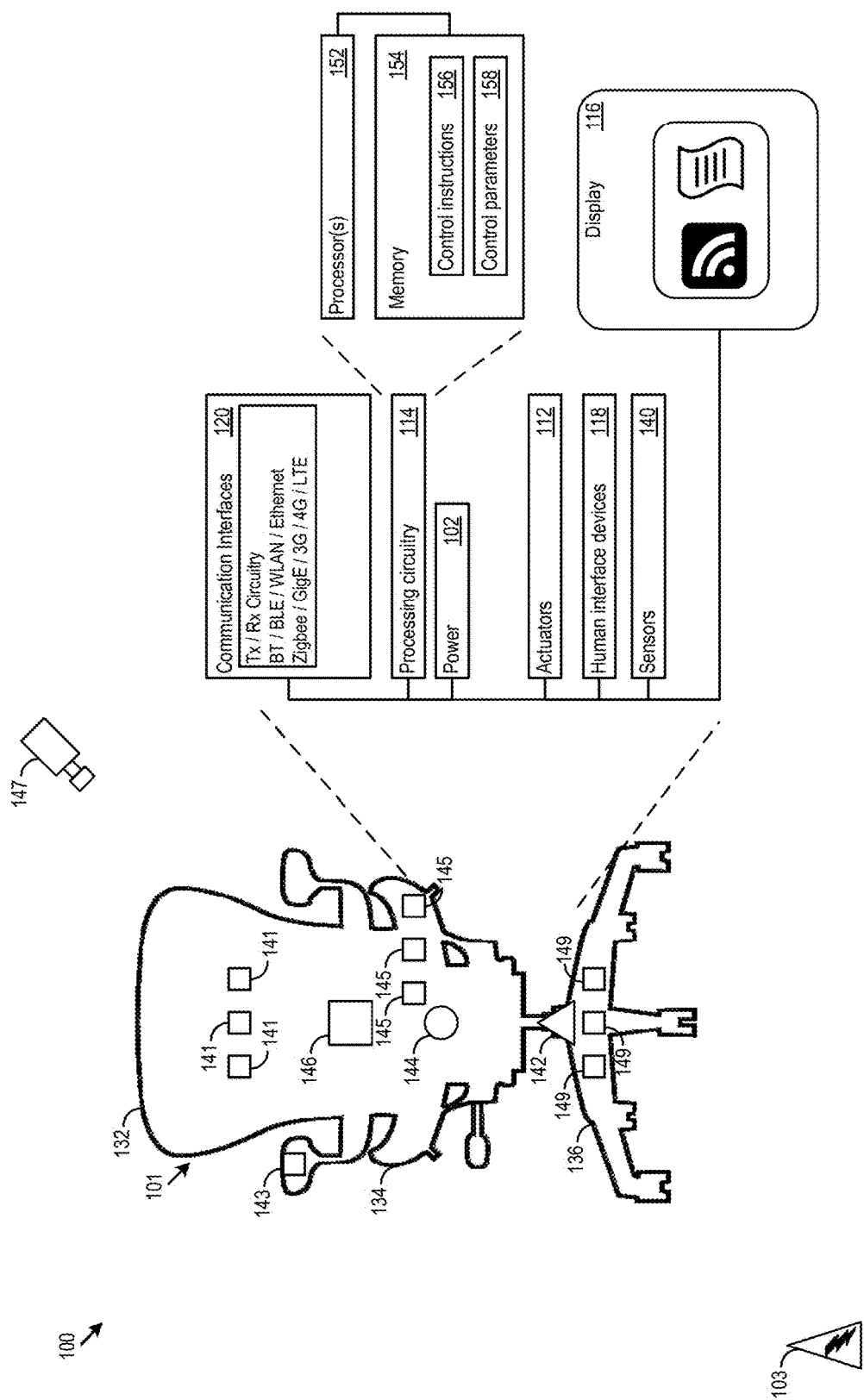
FIG. 1 shows an example office productive structure (OPS).

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Described below is a context-aware architecture that may be integrated with office productivity structures (OPSs), such as task chairs, executive seating, other office seating, tables, workstations, desks, shelves, other furniture, room lighting, task lighting, climate control systems, storage devices computer docks, computer internet portals, telephone switchboards, wearable posture sensors, and/or other OPSs. Sensors within the OPSs may identify signatures, such as gestures, biometric data, circadian timings, posture states, positioning information, noise levels, temperature, orientation information, facial expressions, identification codes, data, posture, pose, or gesture durations, and/or other signatures. The sensors may also provide data to a local or remote analysis system that performs the identifications. The OPSs may also communicate with analytics systems, such as enterprise databases, local databases, servers, network systems, cloud analytics systems, and/or other processing systems, to facilitate, as just one example, generation of a representative productivity model for one or more operators utilizing the OPSs. The productivity model may be integrated with operator data and applications, such as email, instant messaging, calendar and/or location applications or data to determine a context for the productivity model and provide context informed feedback to the operator.

Based on the productivity model, the analytics system may determine productivity information that may be of use to the modeled operator. For example, the productivity information may include helpful tips such as break timing, mappings in performance versus time of day, suggested meeting locations and times, goal status, posture adjustments, indications of OPS designs or configurations better suited to the operator's use profile, and/or other tips. The information may be presented to the operator via push notifications, data visualizations, and/or other data displays to a mobile device, terminal, workstation, and/or other operator device. The analytics system may also be capable of learning through operator feedback. For example, some observations may be acted upon while others are ignored. The application may tailor its observations based on characteristics of those that are acted upon to increase the chance of user response to observations.

Additionally or alternatively, the productivity information may be used to support enterprise application interactions, such as loading programs upon arrival, limiting electronic distractions (e.g., calls, emails, or other during periods of high productivity), loading to-do lists, executing time logging applications, notifying security or safety systems of occupancy, and/or other enterprise application integration.

In various implementations, the productivity model may include data on informal and/or official hierarchical dynamics within an organization. For example, by monitoring meeting locations (e.g., a tendency of one employee to travel to another's office for meetings) a system may determine status relationships among the employees within the company. For example, for longer scheduled meetings it may be common for a lower ranking employee to travel to the office of a higher ranking employee. Using captured meeting data from chair occupancy states, calendar data, and/or data sources, the analytics system may determine hierarchical states within an enterprise and/or other organization. The hierarchical state may be integrated into the productivity model.

The analytics system may also provide OPS maintenance monitoring. Data collected by the OPSs may be used to determine the current condition of the OPSs. For example, posture and weight distribution data from a chair may indicate that a spring or other biasing member has worn out. In the example, the chair may recline more than a determined tolerance range would allow because of the worn out spring. This condition may be diagnosed from the data and the analytics system may send out a notification that the chair should be replaced or serviced. Other maintenance diagnoses for OPSs may be made via the collected data.

FIG. 1 shows an example OPS 100. The example OPS 100 is a task chair. However, other OPS types may be used in conjunction with the architectures and techniques described below. Many of the structural elements and functionalities (e.g., actuators) described below for the OPS 100 are optional, but may be included in support of sensing and feedback capabilities described further below.

The OPS 100 may include a power source 102, and one or more electrically powered devices 110 coupled to the power source. The power source 102 may include a battery, fuel cell, capacitor and/or capacitor bank, photovoltaic cells, and/or other power sources. The power source 102 may be attached to a mobile portion 101 of the OPS, wireless transmit power from a station 103, or be connected via wired tether to the mobile portion 101. Where wires or cables are used, such tethers may be removed from view and from potential pedestrian traffic, for example, through concealment under carpeting, walls, wainscoting, conduits, wire management devices, or other places of concealment. The station 103 may include a charging station for the mobile portion 101. The mobile portion may use motive systems to travel to the charging station during periods of non-use. In some cases, charging arms or other extenders may fold out from the mobile portion 101 or charging station to charge the mobile portion during periods of non-use.

The electrically powered devices may include one or more actuators 112 for adjustment of OPS configuration and positioning within a room or location, processing circuitry 114 to support application execution on the OPS, displays 116 for presenting information to operators, human interface devices 118, networking interfaces 120, and/or other electrically powered devices. The actuators 112 may include motive devices, electromotive devices, electrical devices, chemical devices, hydraulic devices, pneumatic devices, electrochemical sources, and/other sources of mechanical energy. For example motors, gears, wheels, engines, or other motive systems may be used.

In a seating-type OPS, such as the example OPS 100, the OPS may include seating structural features such as a backrest 132, which is coupled either directly or indirectly to the seat 134 and/or to the base 136. In some cases, the actuators 112 may be capable of executing automatic adjustment of the seat 134, backrest 132, base 136 or other portion of the example OPS 100. Further, automatic adjustment mechanisms can be implemented to adjust other structural features, including seat depth, armrest height, lumbar pressure, lumbar position, sacral support, spinal support, cranial support, thoracic support, foot support, leg support, calf support, and/or other seating support. For example, a seating-type OPS may include adjustment features to achieve a full range of positions from a seated to a reclined to a standing position.

The actuators 112 may be coupled to processing circuitry 114. The processing circuitry 114 may be further coupled to sensors 140 within the OPS 100. The sensors 140 may include accelerometers 142, load sensors 144, temperature sensors 146, and/or other sensors. The sensors 140 may be grouped within different positions within the OPS 100. For example, backrest sensors 141 may be used to determine a position parameter for the backrest 132 such as, for example, seat back tilt relative to base, back weight distribution and rate of recline. The sensors may include accelerometers, strain gauges, load cell sensors, pressure sensors, and/or other sensors. Seat sensors 145 may determine occupancy positioning within the seat through a position parameter of the seat 134 such as, for example, the seat pan weight distribution, seat pan tilt relative to a horizontal level (e.g., the floor), seat pan height relative to the floor, and/or other metrics. The seat sensors 145 may include accelerometers, strain gauges, pressure sensors, load cell sensors, laser ranging sensors, other ranging sensors, and/or other sensors. In addition, backrest sensors 141 and seat sensors 145 may cooperate to determine the occupancy state of the seat. Base sensors 149 may also determine a position parameter of the base 136 such as, for example, rotation, distance of travel, impact force, orientation with respect to a desk or other object, distance from other objects, weight differential on feet, and/or other physical states. The base sensors 149 may be used to measure chair movement and position, and feet position. The base sensors 149 may include magnetometers, gyroscopes, optical position trackers, dead reckoning calculators, accelerometers, ultrasound systems, ranging systems, optical cameras, and/or other sensors. Armrest sensors 143 may measure the force on the armrest, and/or the orientation of the force vector on the armrest to determine arm posture. Further, differentials between armrests may be used to determine sideways slouch and/or other posture conditions. In the illustrated embodiment, the seating-type OPS 100 includes a first armrest and a second armrest. A first armrest sensor coupled to the first armrest detects a first force acting on the first armrest. A second armrest sensor coupled to the second armrest detects a second force acting on the second armrest. Detecting the first force and the second force may include detecting a magnitude and direction associated with each force. Furthermore, a difference between the first force and the second force can be used to determine the differential mentioned above. A particular posture or posture condition can then be detected based on the difference (i.e., the differential) between the first armrest and the second armrest. Armrest sensors 143 may include strain gauges, pressure sensors, and/or other sensors. Additionally or alternatively, off-OPS sensors 147 may be used for monitoring the OPS 100 from a distance. Off-OPS sensors 147 may include ranging systems, video cameras, motion sensors, gesture recognition systems (e.g., Xbox(™) Kinect(™), and/or other gesture recognition systems), and/or other sensors.

The OPS 100 may include any number of a wide variety of sensors 118, and several examples are given in Table 1.

TABLE 1

Sensor Type and Position.

| Sensor Position | Sensor Type |
| --- | --- |
| Backrest | accelerometers, strain gauges, pressure sensors, load cell sensors, laser ranging sensors, other ranging sensors |
| Seat | accelerometers, strain gauges, pressure sensors, load cell sensors, laser ranging sensors, other ranging sensors |
| Base | magnetometers, gyroscopes, optical position trackers, dead reckoning calculators, accelerometers, ultrasound systems, ranging systems, optical cameras |
| Armrest | strain gauges, pressure sensors |
| Off-OPS | video cameras, motion sensors, gesture recognition systems |

As explained above, at least some of the sensors 140 detect a physical force imparted by the user (e.g., a seat pan weight distribution, a backrest weight distribution, armrest force vector, etc.) on the seating-type OPS 100. Each sensor 140 then generates an output signal indicative of the physical force. The sensors 140 may detect rotational movement, recline, lateral positioning of seated individual, the pointed direction of the seat (north, south, east, west, and/or other intermediate directions), noise levels, temperature levels, and/or other conditions. In particular, the output signals from the sensors 140 and the position parameters determined for the chair are used to determine a current posture of a user sitting in the chair as discussed above.

In various implementations, OPSs may not necessarily include one or more of the above features. For example, an OPS may include sensors and communication capabilities and might not include actuators and/or local analytic processing. The sensors 140 may additionally or alternatively be communicatively coupled to an analytics system such that the OPS may collect sensor data and transmit the collected data to an analytics system, e.g., a cloud based analytics system. The data and/or generated observations may be sent from the analytics system back to an operator device, e.g. smartphone, computer, OPS display, and/or other operator device.

The processing circuitry 114 may execute instructions that may adjust the OPS 100 until certain sensor criteria are met. For example, a threshold tolerance load may be allowed on the seat 134 for a certain operator, as detected by a load sensor 144 in the seat 134. The processing circuitry may cause the actuators 112 to adjust the OPS structural configuration to shift weight between the seat 134 and the floor. Alternatively or additionally, orientation criteria may be probed using accelerometers, positioning criteria may be determined using ranging technologies, satellite navigation (e.g., GPS, GLONASS, GALILEO, and/or other satellite navigation), or other positioning technologies. However, the adjustment instructions, adjustment criteria and sensor usage may vary widely. Further, the processing circuitry may receive adjustment instructions or indications of an adjustment routine over the network interface from a analytics system. The instructions and/or indications may be related to applications running on the analytics system, such as maintenance applications, enterprise applications, and/or productivity assistance applications.

The processing circuitry 114 may include one or more processors 152 (e.g., general purpose processors, central processing units (CPUs), graphics processing units GPUs, application specific integrated circuits (ASICs), audio processors, field programmable gating arrays (FPGAs), microcontrollers, multi-core processors, and/or other integrated processing circuitry). The processing circuitry 114 may further include a memory 154. The memory 154 stores, for example, control instructions 156 that the processor 152 executes to carry out desired functionality for the OPS 100. For example, functionality may include OPS structural adjustment, maintenance functions, enterprise application interaction, and/or other functions. The control parameters 158 provide and specify configuration and operating options for the control instructions 156. Control parameters 158 may include adjustment configuration data, enterprise application data, sensor data, actuator position data, and/or other control parameters.

The OPS 100 may also include network interfaces 120, which may support wireless, e.g., Bluetooth, Bluetooth Low Energy (BLE), ZigBee, Wi-Fi, WLAN, cellular (4G, LTE/A), and/or wired, ethernet, Gigabit ethernet, optical networking protocols. The network interfaces 120 may allow communication with the analytics system 200, other OPSs, and/or other devices.

The OPS 100 may include different positioning and adjustment configurations for different operators. For example, two operators using the same OPS may have different associated settings. In some cases, OPSs may identify different operators based on signatures or other identifiers as described below. In some cases, a single operator may have multiple OPS configurations applied in different situations, which may also be identified by signature. For example, a relaxed position may be used in times of habitually high productivity (e.g., during a portion of an employee's prime working hours of a given day) to promote operator comfort, but an upright or more standing type position may be used at times of habitual drowsiness. Thus, an increasingly active stance may be used to maintain high output by the operator. The control parameters 158 may store one or more configuration settings for the operators.

Figure 16:
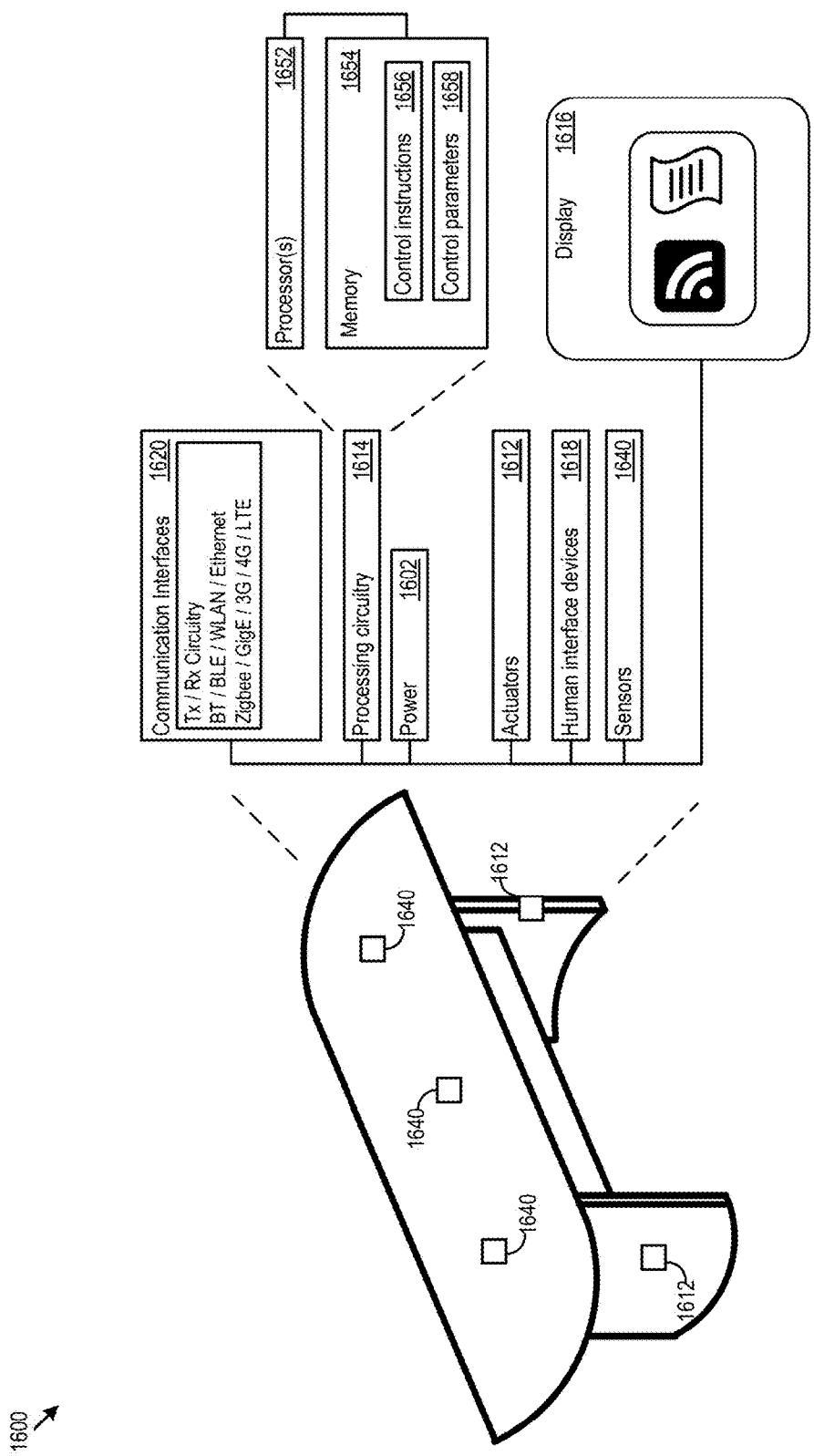
FIG. 16 shows a second example OPS.

Turning ahead to FIG. 16, that Figure shows a second example OPS 1600. The example OPS 1600 is a table. For example, the OPS may be implemented as a table in a conference room or desk in an office. The OPS 1600 may include power sources 1602, processing circuitry 1614, displays 1616, human interface devices 1618, network interfaces 1620, actuators 1612, sensors 1640, or other components.

The second example OPS 1600 may use power sources 1602, processing circuitry 1614, network interface 1620, human interface devices 1618 and displays 1616 similar to those present in the example OPS 100. However, the capabilities of the components in the second example OPS 1600 may differ from those of the OPS 100.

The processing circuitry 1614 may include one or more processors 1652 (e.g., general purpose processors, central processing units (CPUs), graphics processing units GPUs, application specific integrated circuits (ASICs), audio processors, field programmable gating arrays (FPGAs), microcontrollers, multi-core processors, and/or other integrated processing circuitry. The processing circuitry 1614 may further include memory 1654. The memory 1654 stores, for example, control instructions 1656 that the processor 1652 executes to carry out desired functionality for the OPS 1600. For example, functionality may include OPS structural adjustment, maintenance functions, enterprise application interaction, and/or other functions. The control parameters 1658 provide and specify configuration and operating options for the control instructions 1656. Control parameters 1658 may include adjustment configuration data, enterprise application data, sensor data, actuator position data, and/or other control parameters.

The actuators 1612 and the sensors 1640 may be customized based on application. For example, the table may include actuators to support height adjust in response to a detected person or signature. The sensors 1640 may include virtually any of the sensors discussed above with respect to the OPS 100. Further, the sensors 1640 may coordinate with actuators 1612 to perform height adjustments based on person size, posture, or position. The OPS 1600 may respond to multiple detected persons. For example, the OPS 1600 may perform height adjustment to adapt to an average height for a group. Alternatively or additionally the OPS 1600 may perform height adjustment to adapt to an extrema for a group. For example, the height adjustment may account for a shortest detected member of a group. Enterprise interaction may also be implemented on the OPS 1600. For example, the OPS 1600 may reconfigure to accommodate an upcoming meeting, actuators 1612 may break apart or join table sub-units, height adjustments may be made based on expected attendees, a message requesting additional seating may be sent by the OPS 1600.

Figure 2:
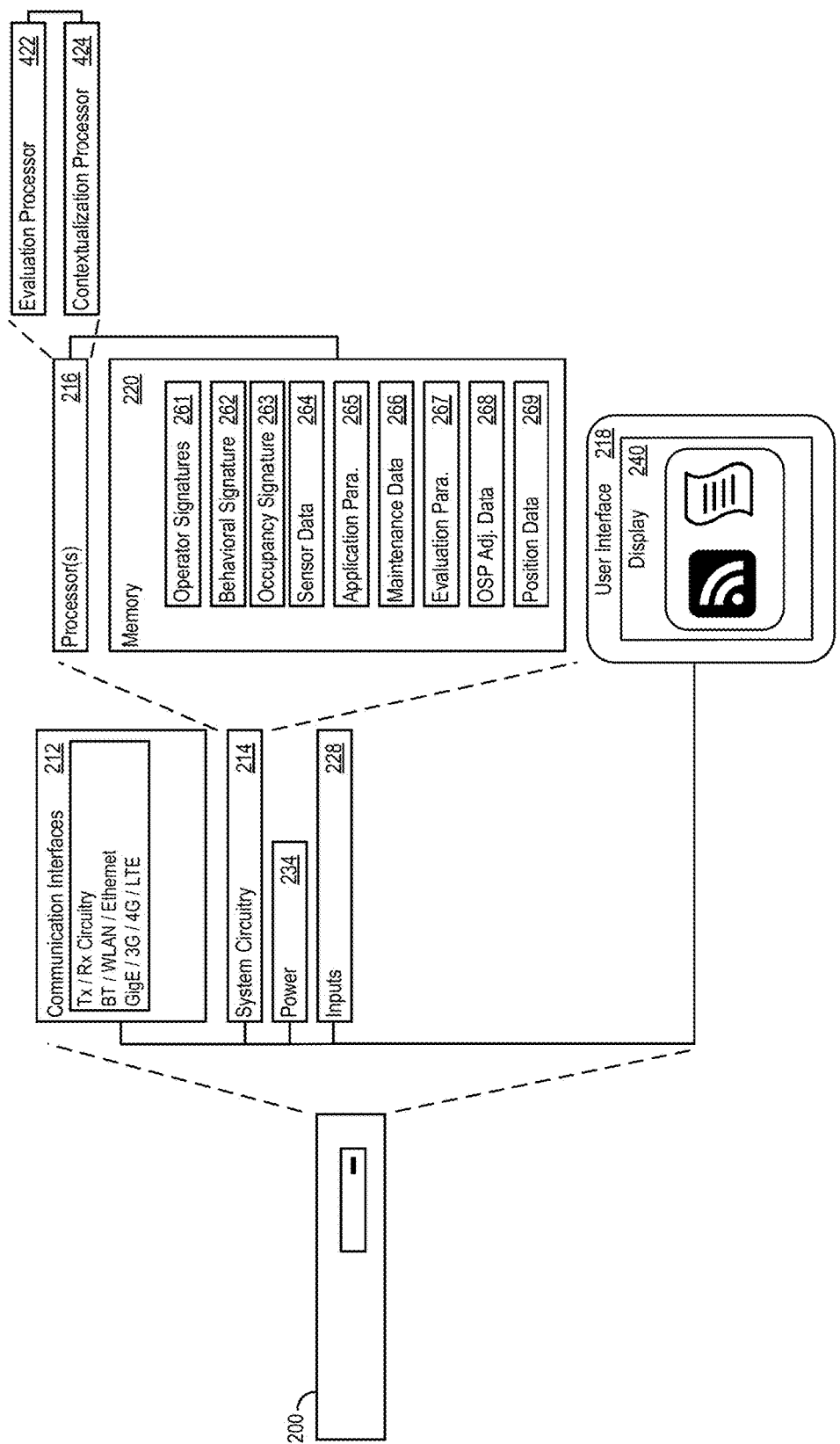
FIG. 2 shows an example analytics system.

FIG. 2 shows an example analytics system 200. The analytics system 200 may include system circuitry 214 to support execution of the functionality described above. The system circuitry 214 may include processors 216 (e.g., graphics processing units, general purpose processors, audio processors, and/or other processing devices), memory 220, and/or other circuitry. The processors may include evaluation processors 422 and contextualization processors 424 as described below.

The memory 220 may store sensor data from OPSs, parameters for evaluation, human resource data identifying operators of OPSs and their jobs or roles, application parameters for enterprise application integration, and/or other data. For example, the memory 220 may store operator signatures 261, behavior signatures 262, occupancy signatures 263, sensor data 264, application parameters 265, maintenance data 266, evaluation parameters 267, OPS adjustment data 268, position data 269 (e.g., previously detected postures for the user), and/or other data to support OPS interaction and data processing. This data may be stored on the memory 220 periodically to remain current.

The analytics system 200 may be implemented in a cloud environment and may be distributed over one or more computing platforms and/or virtual machines. In some cases, the analytics system may be dynamically instantiated such that particular hardware units may be interchanged from instance to instance.

The analytics system 200 may also include communication interfaces 212, which may support wireless, e.g. Bluetooth, Wi-Fi, WLAN, cellular (4G, LTE/A), and/or wired, ethernet, Gigabit ethernet, optical networking protocols. The communication interfaces 212 may allow communication with OPSs and among computing platforms hosting various computational portions of the analytics system 200. The analytics system 200 may include power functions 234 and various input interfaces 228. The analytics system 200 may also include a user interface 218 that may include human interface devices and/or graphical user interfaces (GUI). The user interface may include a display 240 to present video, images, and/or other visual information and/or to the operator. In various implementations, the GUI may support portable access, such as, via a web-based GUI. Functional aspects of the analytics system 200 are described in connection with other Figures below.

Figure 3:
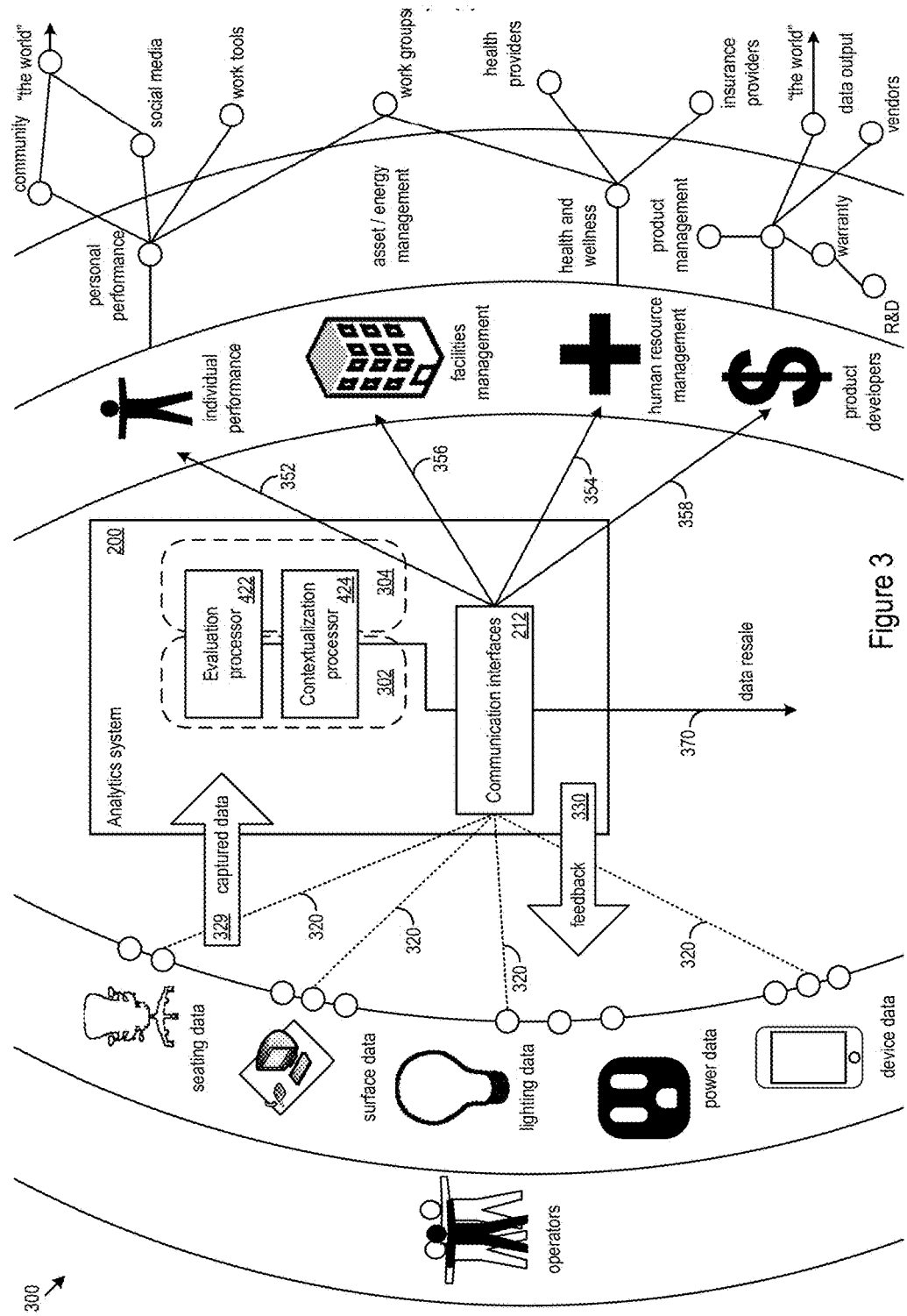
FIG. 3 shows an example OPS environment.

FIG. 3 shows an example data communication environment 300. The analytics system 200 is present in the data communication environment 300. The contextualization processors 424 and evaluation processors 422, described below, may be part of algorithmic engine circuitry 302 and the application framework circuitry 304. The communication interfaces 212, may communicate with the OPS sensors for collection of various sensor data 320. For example, seating data (e.g., gestural data, postural data, spatial data, OPS model data, and/or other seating data), surface data (e.g., vibrational data, pressure data, spatial data, and/or other surface data), building data (e.g., auditory data, light usage data, power consumption data, security system data, heating/cooling data, temperature data, motion sensor data, and/or other lighting/power data), device data (e.g., personal computer (PC) application data, smartphone data, location data, calendar data, enterprise application client data, fitness monitor data (Nike(™), Jawbone(™), Fitbit(™), and/or fitness devices), wearable posture detection device data (e.g., LumoBack, and/or other wearable devices), and/or other data). The analytics system 200 may provide feedback 330 to the OPSs via new configurations (e.g., seating settings, other OPS settings, lighting states, heating/cooling states, other autonomous building feedback, enterprise application server data, and/or other feedback).

The interface 212 may also provide data outputs to various enterprise application management systems. For example, the analytics system 200 may send personal performance feedback 352 to individual users via various channels, such as social media, enterprise application server data, human channels (e.g., spurring a co-worker to provide encouragement to an operator in the same workgroup, or other human interaction). In another example, the analytics system may send human resources information 354 (e.g., health and wellness information, social interaction data, and/or other human resource data). Human resource data can be used to co-ordinate with external vendors such as health care providers, insurance providers, and/or other external service providers. In some cases, data may be anonymized to protect individual privacy, but allow integration with external providers at an enterprise level. The analytics system 200 may integrate with building controls for site/asset management 356. Additionally or alternatively, product providers may access product data 358 to aid in research and development, product management, warrant management. In some cases, third parties may be interested in OPS data (e.g., manufacture dates/location, serial numbers, usage data), opportunities for data resale 370 may arise. The opportunities may be attractive for organizations in need of custom solutions and potential discounts in overall monitoring system deployment costs. Third-parties may be given different levels of OPS data depending on the third-party application, the subscription level of the third-party, data privacy concerns of the operators, data sharing priorities of the data collecting organization, or other business concerns. In some cases, sensor data may be filtered and sent to the third-party. Additionally or alternatively, data may be processed and actionable insights may be sent to the third party.

Figure 17:
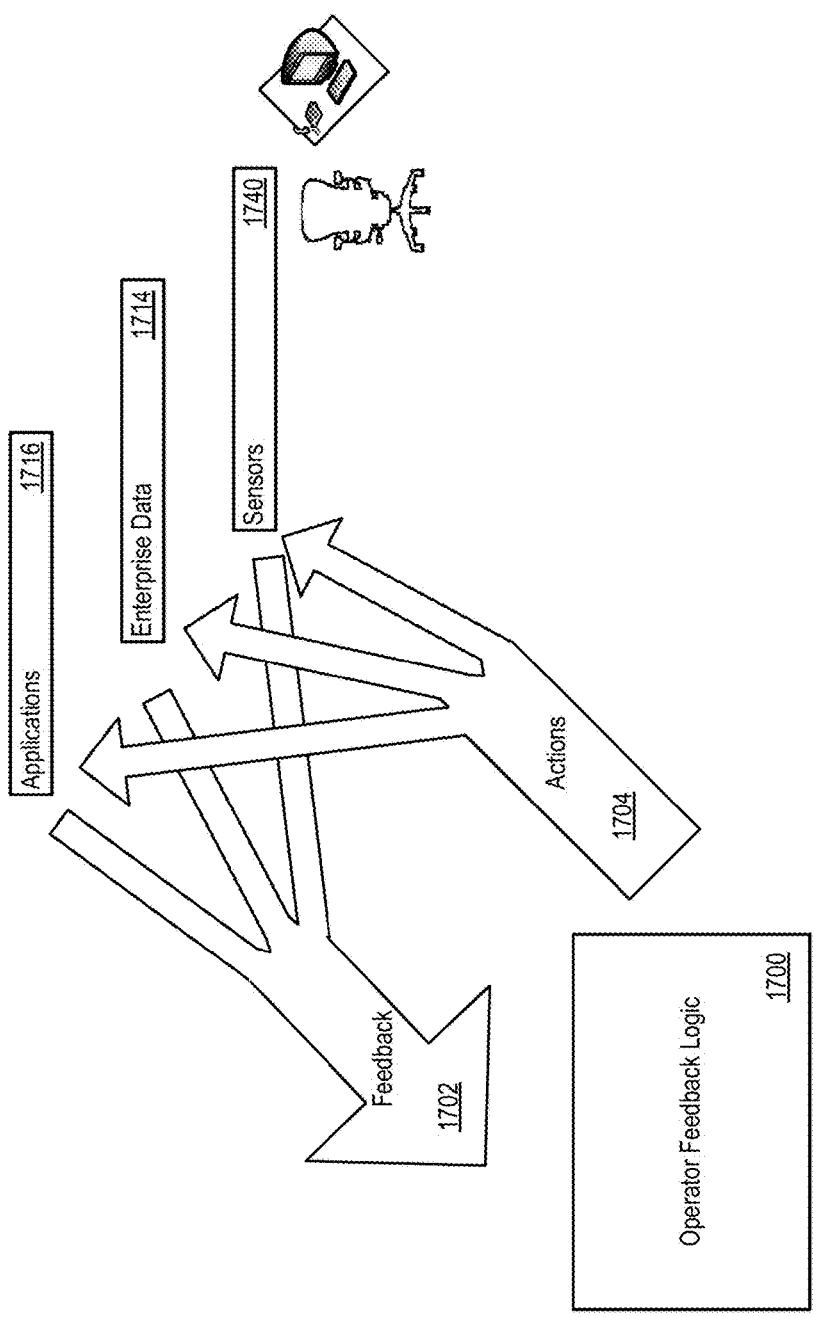
FIG. 17 shows example operator feedback logic.

FIG. 17 shows example operator feedback logic 1700. The feedback logic may collect feedback 1702 from an operator via OPSs sensors 1740, enterprise data 1714, application integration 1716, or other channels. For example, a chair type OPS may receive a stress profile from the chair sensors. The operator may shift his/her weight in response to a notification transmitted to a display or other action by the system. For example, the operator feedback logic 1700 may generate a command message that causes the chair actuators to alter the orientation of the chair, which may cause the stress profile to change. Additionally or alternatively, the operator feedback logic 1700 may generate a push notification for the operator's mobile device (e.g., and transmit the push notification to be the display of the operator's mobile device). The push notification may indicate a target posture to the user and request that the operator shift/change postures. The system may interpret the resulting stress profile after the shift as feedback from the operator (i.e., the system may determine whether the user moved toward the target posture, away from the target posture, or no movement was performed). In another case, the operator may provide express feedback through enterprise software or other applications. For example, the operator may logon to an enterprise portal and provide feedback thorough tools available on the portal. Additionally or alternatively, the operator may provide feedback through enterprise applications that run on the operator's device with or without express logon.

In some cases, the enterprise logon portal may be integrated with other online portals and resources. For example, enterprise resources may be accessed through social media, employee management sites or other online resources.

The operator feedback logic 1700 may respond to the feedback with actions 1704. The actions may be directed to actuators or displays associated with any of the feedback input channels. The action need not necessarily be sent back through the specific channel or channels on which the feedback that initiated the response originated.

In some implementations, an OPS may include one or more features of the ergonomic office chairs. One example is sold under the tradename AERON® by Herman Miller of Zeeland, Mich. Features of AERON® chairs that may be incorporated into chairs include seats and backrests with a form-fitting, breathable woven mesh membrane; one-piece carrier members for securing the periphery of the woven mesh membranes to the chair frames; mechanisms for controlling tilt range and resistance to tilting; and linkage assemblies by which seats and backrests may pivot about hip pivot points while simultaneously tilting rearward. However, other chair and OPS designs may be used that may additional or fewer adjustment options. Another example may be sold under the tradename PostureFit® also by Herman Miller of Zeeland, Mich.

OPSs may be equipped with integrated or add-on sensor/communication units to furnish processing circuitry, sensors, and/or communication interfaces. These units may cooperate in the monitoring and signature recognition features described here.

In some implementations, a sensor device may be added to an existing OPS to facilitate monitoring features. In an example system, a seating senor may be 2 in×1 in×¾ in and have sensors capable of measuring movement, recline, time, temperature vibration, pressure, and/or other conditions. The sensor device may be battery operated. The sensor device may communicate with a terminal or other OPS via Bluetooth, BLE, and/or other communications protocols. The terminal or other OPS may forward collected data to the analytics system 200 for analysis. In some cases, the sensor device may establish a direct communication link to the data processing device over Bluetooth or other communication protocols.

In some cases, the monitoring system may be used to determine informal and/or formal group dynamics (e.g., hierarchical organization, social groupings, and influence within an organization). As part of the determination group dynamics, an occupancy or space use study may be performed. In some implementations, an operator may provide a list of spaces, such as a floor plan, which are to be monitored for the study. However ranging and navigation sensors on OPSs may be used to determine the space layout. These spaces are then stored in database tables in a database where they can be assigned identifiers and associated with operators and/or other individuals. For example, an office room may be associated with one or more occupants and given an identifier. OPSs may include serial numbers or other identifiers. The position of the OPSs within the studied space may also be determined.

In various implementations, OPS connectivity may be managed throughout an organization. For example, an OPS may serve a local hub for connectivity for other satellite OPSs. For example, a workstation unit may have access to wide area network (WAN) connectivity. The workstation may communicate with other OPSs via a second communication technology. For example, the workstation may use WIFI, Bluetooth, other wireless connectivity, and/or wired connections to communicate with other OPSs. In some cases, OPSs may have differing sensing and processing capabilities. Satellite OPSs may collect data via onboard sensors and send the captured data to a central OPS for processing and/or application integration. The central OPS may further interact with the analytics system over WAN or other network connectivity. In some cases, OPSs need not necessarily directly exchange data with other OPSs. For example, an OPS may utilize onboard data processing, onboard sensing, and onboard network connectivity to maintain a communication link to the analytics system.

The OPS data may be logically associated with the OPS sensors which collected the data, e.g., through database keys and fields. However, for some OPS configurations, data association may occur in accord with application options. For example, a ranging measurement of an office room may be associated with the OPSs located within that office room, even if the scan was performed by another OPS or a survey device that not connected to an OPS. The logical association may be maintained at the analytics system. Additionally or alternatively, indicators for data association may be generated by OPSs and sent along with the data (e.g., as metadata, or other data) to the processing system. The data may be sent to the analytics system via transmission processes and systems, such as Hypertext Transfer Protocol (HTTP) operations (e.g., POST, GET, PUT, DELETE, and/or other operations) to send)ML data to a Web Service, utilizing socket communication to send messages, cloud storage operations on Cassandra or Hadoop systems, and/or other processes. Some system implement transfers with security layers at various links between data collection at an OPS sensor. For example, secure socket layer (SSL), secure file transfer protocol SFTP, virtual private network tunnels, and/or other encrypted transfer protocols.

Figure 4:
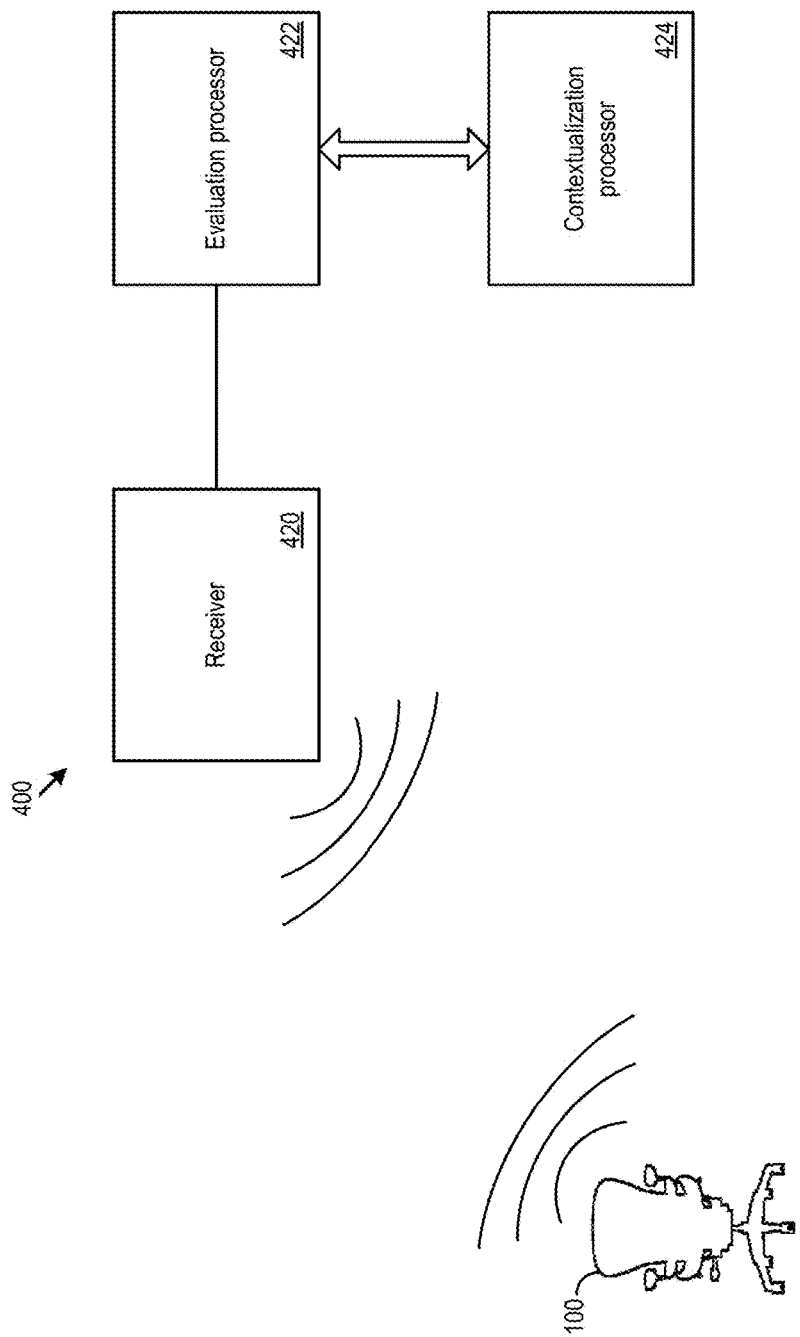
FIG. 4 shows an example system for monitoring and analyzing occupancy signatures.

FIG. 4 shows an example system 400 for monitoring and analyzing occupancy signatures. The example system determines occupancy within one or more physical spaces. The physical spaces may include physical elements, such as seats or work surfaces or other OPSs. The example system 400 may be implemented on the one or more analytics systems 200 as described above. The system includes a receiver 420 and an evaluation processor 422 and contextualization processor 424. The receiver 420 is operative to receive use information, such as estimated or probable utilization states. Probable utilization states may be determined over a first period of time, such as minutes, hours, days, or other period of time, for the physical elements, e.g., seat or work surface. The determination may be based on magnitude values for movement of the physical element during a discrete portion of the first period of time, e.g., a 15 second interval or other interval. The probable utilization state is indicative of a likelihood that at least one occupant is utilizing the one physical element, e.g., sitting in the seat or working at/on the work surface, and therefore occupying at least a portion of the first physical space during the first period of time.

The system 400 further includes an evaluation processor 422 and contextualization processor 424. The evaluation processor 422 is coupled with the receiver and operative to evaluate at least a portion of the received portion of determined probable utilization states to determine a number of occupants occupying at least a portion of a physical space. For example, the evaluation processor 422 may determine whether an occupant is likely to have caused the movement based on the associated probable utilization state that was determined. Additionally or alternatively, the evaluation processor 422 may combine the received data from multiple OPSs 100 and/or receive additional inputs, such as the status of the lights in the room, historical security badge reports, motion detector reports or other data which may be used to confirm that the probable utilizations states are in fact indicative of an occupant as opposed to false positives.

The contextualization processor 424 may be coupled with the evaluation processor 422 and compare the determined number of occupants to data from expected occupancy models, human resources data, previous measurements, or other data to facilitate management of the occupancy of the first physical space. For example, the contextualization processor 424 may determine occupancy of at least a portion of the first physical space at a specific time based on at least the received determined probable utilization states and demonstrate utilization of the portion of the first physical space at the specific time. In another example, the contextualization processor 424 may determine occupancy of at least a portion of the first physical space at a plurality of specific times based on at least the received determined probable utilization states and demonstrate a change in occupancy of the portion of the first physical space over a period of time encompassing the plurality of specific times. In another example, the contextualization processor 424 may correlate occupancy of at least a portion of the first physical space to at least one event based on at least the received determined probable utilization states. In another example, the contextualization processor 424 may compute an index value representative of at least the received portion of the plurality of probable utilization states.

In another example, the contextualization processor 424 may correlate occupancy of at least a portion of the first physical space to at least one attribute thereof based on at least the received determined probable utilization states, wherein the attribute may include location, environmental conditions (e.g., temperature, vibration, relative humidity, concentrations of allergens or volatile organic compounds, atmospheric pressure, radiation, electro-magnetic fields, etc.), available amenities, decor, electrical consumption or combinations thereof. In another example, the contextualization processor 424 may aggregate the received determined probable utilization states with previously received determined probable utilization states and contextualize at least the received determined probable utilization states based on the aggregation. The previously collected determined probable utilization states may have been received for a second physical space different from the first physical space or, alternatively, the previously received determined probable utilization states may have been received for a second physical space operated by an entity different than that which is associated with the first physical space.

Once occupational data is collected, the contextualization processor 424 may monitor the flow of operators from location to location. The flow of operators may be used to determine where and when meetings occur and who is in attendance. The pattern of meetings may be used to determine informal and/or formal hierarchical relationships within an organization. For example, regular meetings between operators in neutral locations (e.g., break rooms, water coolers, hallways, and/or other neutral locations) may signify an informal "water cooler" relationship. In another example, regular meetings at non-neutral locations, where an operator moves from his/her normal physical space to the physical space of another, may indicate formal organizational relationships.

In some implementations, seating sensors may collect proximal, spatial, temporal, motion, acceleration, and gestural data to facilitate recognition of signatures that may be representative of certain mental or postural states (i.e., a current sitting posture) of an operator. The seating sensors may send these data to the evaluation processors 422 of the analytics system 200 for recognition of the signatures. The contextualization processors 424 of the analytics system 200 may recognize, determine, track, correlate, and/or order these and desired states. In other words, the analytics system 200 may store previous information such as the signals from the seating sensors, mental states of an operator, and/or different postures for an operator. Responsive to the analysis, the contextualization processors 424 may send actionable observations to the operator. These observations may be used to fill experiential blind spots (e.g., alerting an operator to habits the operator may be unaware of or only mildly aware). The actionable observations may be provided through one or more other interface channels described above with respect to the OPS environment 300.

Signatures may include virtually any reoccurring set of observable phenomena that may be used to identify a particular individual, group of individuals, behavior, mental state, and/or other attribute. For example, identifiable motion patterns, radio frequency identification (RFID) tags, a gate while walking, facial images, fingerprints, gestures, daily routines or other habits, biometric data, location data, smartphone or device data, job description, and or other identifiable data. For example, for a gesture-type or a posture-type signature, a seating OPS may detect a chair rotation of 20 degrees with an increased back tilt of 5 degrees with respect to a previous state. When these two detections occur within 3 seconds this may indicate an interruption or task shift. This may be correlated with calendar data, location data, and/or other data to determine high resolution work efficiency analysis. However, other signatures may be correlated and analyzed.

A task shift may occur when an operator switches from performing a first task to performing a second task or switches from first state to a second state. For example, task shifts may occur when an operation switches from typing to a phone conversation and again when shifting from a phone conversation to reflective state. In some cases, a target number of task shifts for a given period may be selected for an operator. However, the target number of shifts may be determined based on the time of day, operator preferences, operator performance history, task shift history, job function, season, and/or other factors.

For individuals, the system may direct actionable observations to focus on an operator centric model. Thus, observations may be directed at the individual operator in a "my world" environment. This may aid in avoiding adding additional distractions to an operator's day through generalized feedback that may not necessarily be applicable to an individual operator. Further, an operator may be able to access OPS specific information to access observations, data, and/or other information associated with OPSs under their own operation. Operators may receive input on improving break timing based on health and/or productivity data. The observations may also assist the user in reducing their own sedentariness and increasing their use of healthy postures. For example, sitting upright too long may be an unhealthy posture. In this example, the analytics system 200 may determine a period of time that the user remain in the current posture (e.g., the upright posture) and generate a notification to a user to change postures when the period of time exceeds a time threshold (i.e., an observation to assist the user in increasing their use of healthy postures). The analytics system may track movement and determine a period of distraction from a grouping of a number of movements over a short period of time (e.g., seconds and/or minutes, or other periods of time). The observations may help an operator become aware of periods of distraction and the time it takes to regain focus.

The system may experiment with various outputs to hone in on improvements to various conditions. For example, a chair type OPS may vary chair orientation to determine which orientations produce desired postures outcomes for an occupant. The OPS may implement random changes. Additionally or alternatively, an OPS may implement a parameter search algorithm to structure the strategy for parameter variation. In some cases, structured searches may identify preferred states after fewer changes when compared to random variation strategies. The iterations of experimentation of and subsequent feedback create a feedback loop. The feedback loop may be managed by the operator feedback logic 1700.

The system may also measure time away from a desk versus time at the desk to determine the ratio of "heads down" to "team time" type work performed in a given day. Thus, the system may assist an operator in decreasing negative distractions (e.g., productivity losses to internet/email usage, or other negative distractions), and increase positive distractions (e.g., team interactions, healthy breaks, posture improving exercise breaks, and/or other positive distractions). In addition, the operator may have the option to share non-anonymized data with health providers for discounts on services and/or premiums. Wearable OPS and wearable notification devices may assist with system functioning during operator mobility situations.

The system may determine actionable observations based on sensor and application data. For example, an observation may include identification of a time in which a down period in an operator's schedule exists. The system may send a notification to the operator to encourage the operator to take a break during the down period rather than waiting for a later time. Additionally or alternatively, the system might warn of an upcoming meeting and assist in locating the individuals attending for the meeting, for example using signatures and occupancy data. The system may also remind you not to take a break when meetings are upcoming. For example, the system may identify a signature indicating an operator may be planning to take a break soon (e.g., motion in chair, habitual information, clearing a to-do-list in an application, and/or other activity). In response, the system may encourage the operator to delay the break to a more appropriate time. The content of a meeting may also affect break timing and content. For example, a walking break may be recommended by the system before a phone-call based meeting, because the operator may not necessarily walk to the meeting. The system may also coordinate information received from multiple OPS. For example, the system may receive input from a conference table OPS that a meeting was a sit-down meeting. Thus, even though operators may have been away from their desk and chair OPS, the system may be able to determine that the time during the conference was still sit-down time for the operators. In some cases, enterprise application data may provide an indicator of the meeting mode. For example, a teleconference or phone meeting may be indicated within the meeting details. Similarly, the inclusion of a specific room or location may indicate that the operator will travel (e.g., within the office or to another site) to the meeting.

Actionable items may be determined by exchanging data with applications. For example, the analytics system may read calendars or task lists from Outlook, or read the type of template presentation from a PowerPoint document to determine a current task of the operator.

In another example scenario, the system may send notifications encouraging activity after lunch rather than sedentary periods. In another situation, the system may also vary the suggested duration of the break based on previous activity levels. For example, the system may encourage an extended break after a long sedentary period. Alternatively, the system may encourage a sedentary break after a long physically active or stressful period. Further, the system may encourage official breaks during periods of low productivity or distraction, for example by monitoring application usage or operator movement. During periods of high productivity (e.g., based on application usage and/or other data), reminders for breaks may be suppressed to avoid taking the operator "out of the zone".

Behavioral data may also be used by the system to facilitate more effective operator interaction with other operators. For example, feedback to vibrational functions of an operator's mobile device may be used to alert the operator that other operators are losing interest in a presentation. The warning may prompt the operator to shift subjects or otherwise rouse the other operators.

To encourage overall health, the system may send notifications to stand up and/or sit down after periods in in either position.

Additionally or alternatively, behavioral data may be correlated with calendar data or other enterprise data. For example, the system may determine operator anxiety levels based on a mix of behavioral observations and upcoming calendar events likely to cause anxiety, e.g., public speaking engagements, job performance reviews, client meetings, meetings with supervisors, or other anxiety inducing events. In some cases, the system may monitor operator behavior around common anxiety inducing events, e.g., events identified by studies or reported by the operator. The behavioral patterns around these known or common anxiety inducing events may be compared to behavioral patterns around other events to identify additional anxiety causing events.

In some implementations, an activity tracker, e.g., Nike (™), Fitbit(™), Apple(™), or other activity trackers, may be integrated with the system. For example, an OPS may establish a link with an activity tracker and access information collected by the tracker. Additionally or alternatively, the operator of the tracker may set the tracker to forward information to the system through another tracker uplink. The tracker data may be used to develop a more holistic view of user activity. For example, the activity tracker may track mobility type fitness, but may have an incomplete picture of an operator's work posture and work activity routines. Integrating the activity tracker data with the OPS sensor data may provide insight into both health at work and health in other spheres.

The system may also analyze the floor plan to determine if the floor plan meets one or more criteria for space usage by an operator or group. For example, space usage goal may include 'per unit' productivity, aesthetics, ergonomics, proximity among specified individuals, accessibility, or other measures. The system may generate command messages for OPS with mobility capabilities, e.g., desks, chairs, tables, lighting, or other OPS to reconfigure the floor plan to meet floor plan goals.

The system may report results from variations in the floor plan or other space usage plans to management systems or personnel. The management systems or personnel may alert space usage priorities responsive to the reports.

Initial configurations and goals may be based on previous studies, industry practices, historical usage patterns, or other data known prior to setup. The initial conditions and data may be altered as current feedback from the system is processed and assimilated.

Figure 5A:
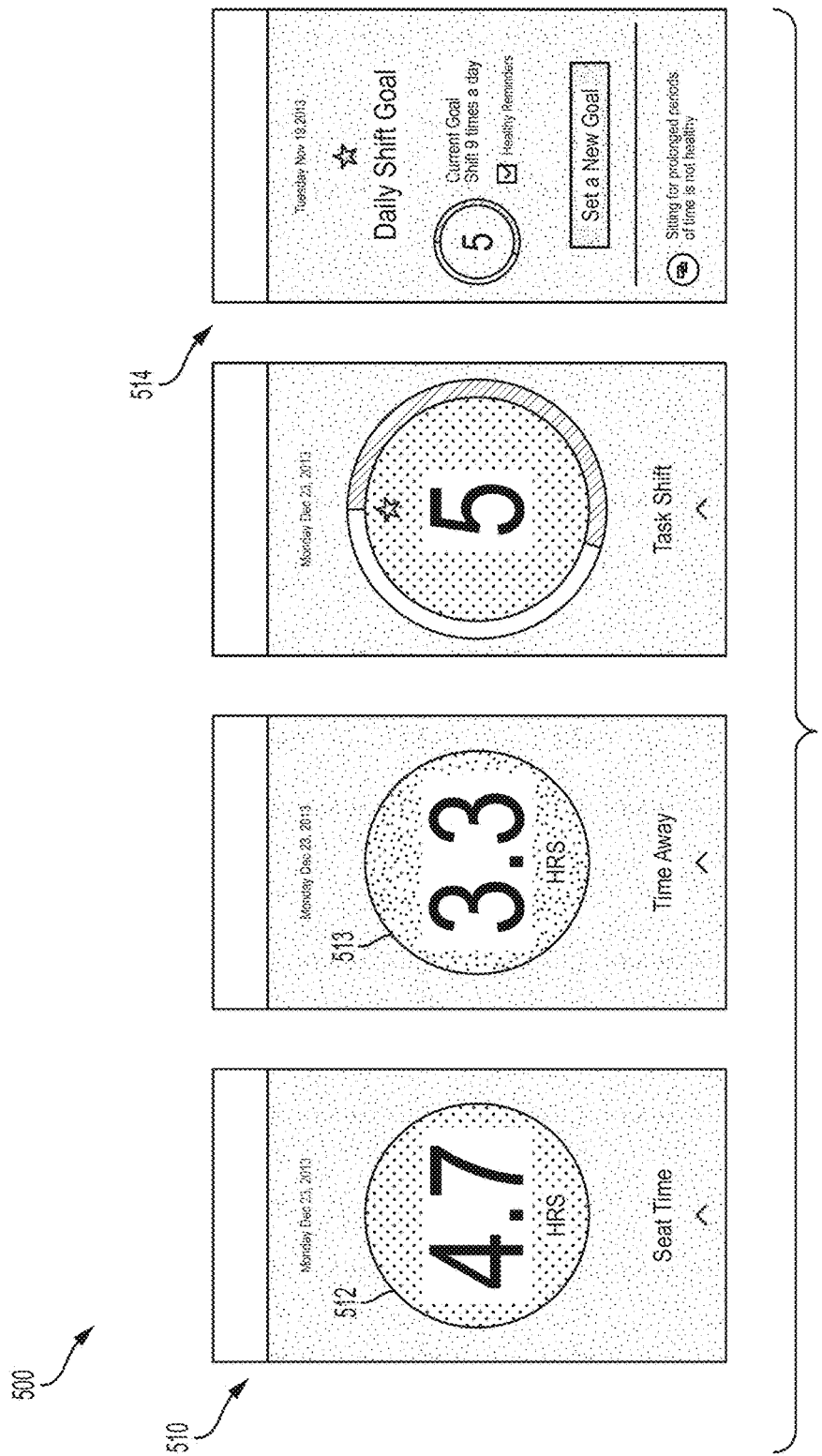
FIGS. 5A-5C show example interfaces for individualized time utilization reports.
Figure 5B:
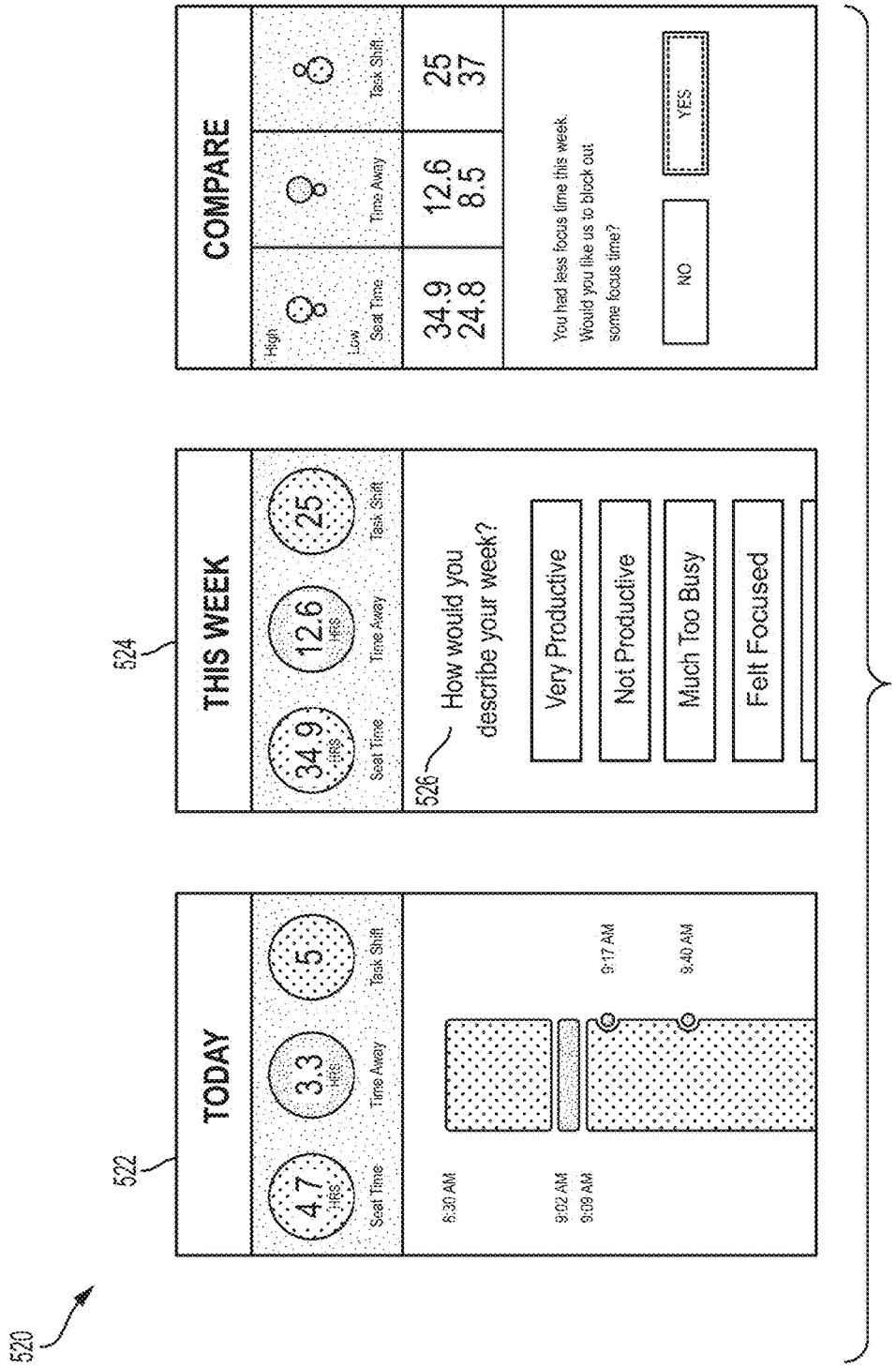
Figure 5C:
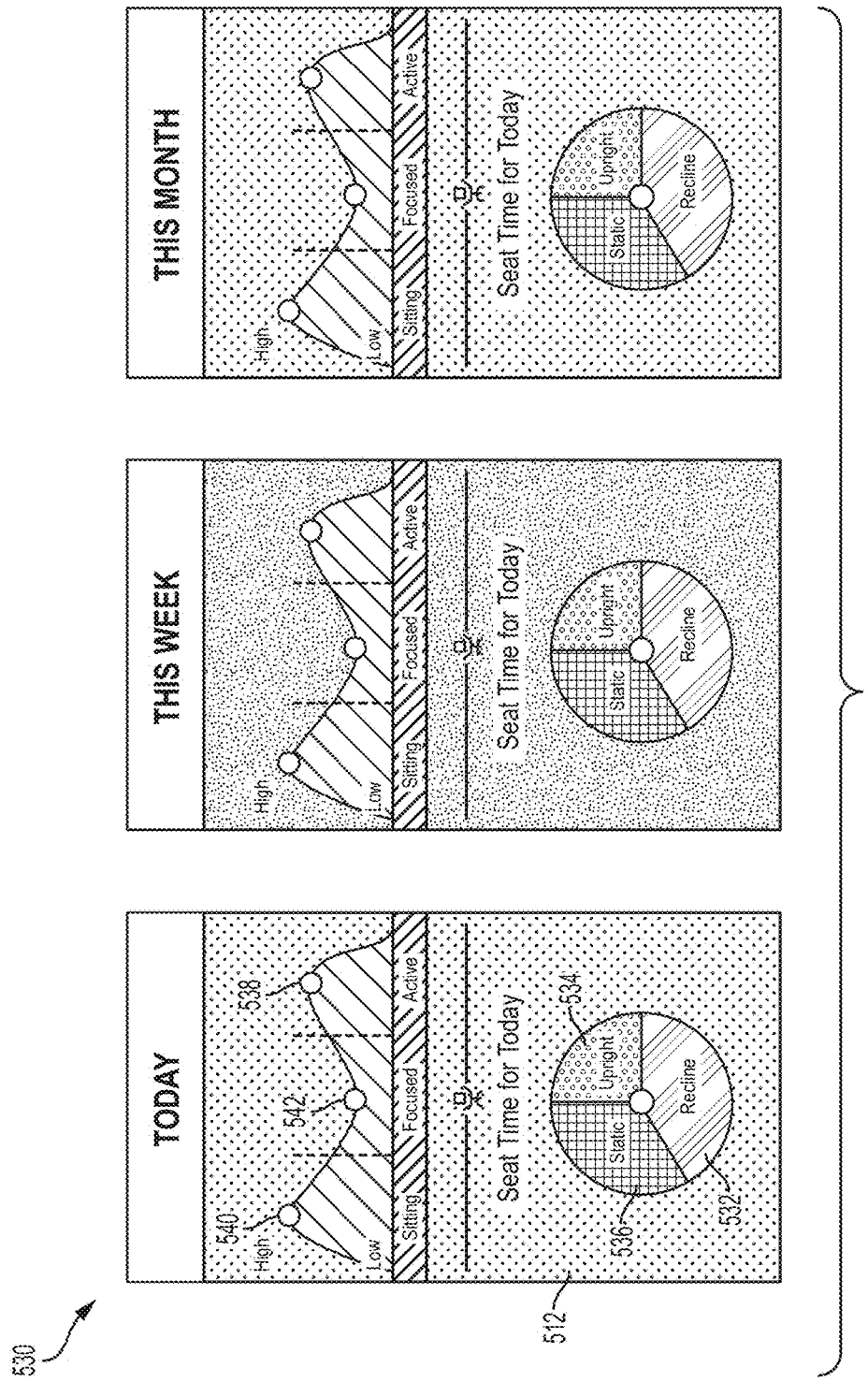

FIGS. 5A-C show an example interface 500 for individualized time utilization reports. The example interface 500 may be generated and displayed by a smartphone application, a console application on a laptop or desktop computer, an application executing on a wearable device, and/or other client computing environments. As shown in FIG. 5A, at the first layer 510, displays of general information on performance (seat time 512, away time 513 ) and/or goal progress 514 may be displayed. The display may use layouts with data visualizations that occupy most of the screen to allow for easy ingestion of the data.

As shown in FIG. 5B, at a second layer 520, which may be accessible for a general menu and/or detail options at the first layer, an operator may access longer term report on daily 522, weekly 524, or monthly trends (i.e., on predetermined periods of time). The reports may place daily performance in context, and allow for cyclical trends to be identified, for example on a daily, weekly, or monthly basis. The second layer may also provide interactive questionnaires 526 for determining an operator's own assessment of productivity. These questionnaires may be sent to the analytics system 200 to adjust productivity models. For example, a generalized productivity model may assume desired productivity may be achieved at a first balance of heads down time to team time. However, an operator's individual productivity balance may differ from the generalized model. Questionnaires may assist that analytics system 200 in assessing that deviation from the generalized model for individual operators.

As shown in FIG. 5C, the third layer 530, which may be accessible for a general menu and/or detail options at the first or second layers, may show a report including detailed information breakdowns for the types of time usage shown at the first layer 510. For example, seat time 512 may be broken into recline 532, upright 534, and static 536 time. In other words, the analytics system subdivides the time spent sitting down into the time spent sitting in different posture classifications such as recline 532, upright 534, and static 536. Each posture classification may include a group of more than one stored posture. For example, the time spent in the recline classification is not necessarily indicative of the time spent in any one particular recline posture, similarly with the upright time 534 and the static time 536. Rather, a plurality of stored postures are grouped together to form one posture classification. Graphs may show performance metrics such as activity levels 538, overall sitting time 540, and focus levels 542. The metrics may assist an operator in determining areas for improvement and areas of strength.

The example interface 500 may show reports of activity posture and environmental sensor data for a predetermined period of time (e.g., a day, a week, a month) as described above. Data displays in the form of sensor/report data versus time may also be used. In the illustrated embodiment, the data is displayed in a pie chart, but other types of graphs may additionally or alternatively be used such as, for example bar graphs, scatterplots, and the like. In the illustrated embodiment, the interface 500 displays a length of time the user spent in each of the stored postures (e.g., recline 532, upright 534, and static 536 ). The peaks and valleys versus time may be analyzed by the system to determine actionable observations. The observations may be pushed to the operator using the interface 500.

The analytics system 200 may generate seat time details (e.g., different postures by the user) by analyzing posture, movement, and/or rotation data collected from chair sensors. The collected data may be correlated and/or cross referenced to activity, operator profile (e.g., age, sex, height, weight, and/or other profile data) location, application usage, calendar, and/or other data collected from sources outside of the chair sensors. Reminders and/or activity goals may be set to help balance activity and focus for healthy productive outcomes. For example, goals may be set to stand up at determined periods. To that end, the analytics system 200 may also include time spent standing in the report shown in FIGS. 5A-C. Goals may also be related to posture, break timing, break content, total sitting time, number of shifting movements, and/or standing time.

The analytics system may generate away time details by analyzing calendar data, seat occupancy data, personnel tracking data, location data, and seat time data away from a primary location. The away data may be compared to seat time data at a primary location. Goals for particular amounts of away time or desk time may be set. In some cases, the healthful nature of the balance between desk and away time may factor into goal setting. For example, the analytics system 200 may suggest a balance that meets company health standards and meeting productivity goal targets for a particular operator.

In some implementations, reports may be sent to an operator's email, e.g., on a periodic basis. For example, they may be sent daily, weekly, monthly, and/or when requested by the operator.

The analytics systems may base decisions to send notifications on lookup tables. For example, the lookup table may include entries organized based on enterprise software, operator, OPS conditions, or any combination thereof, e.g., operation shift frequency, operator alertness, OPS sensor readings, calendar entries, email box fullness, keyboard input rate, or other measures. The lookup table may match the input conditions to an entry and execute an action associated with the entry. In some cases, the entry may instruct the system to send a notification. In some cases, the entry may instruct the system to wait a certain period before performing another lookup check to avoid inundating the operator with notifications. In some cases, the entry may instruct the system to adjust an OPS position setting.

Additionally or alternatively, the system may have one or more default actions when no entries match the current conditions. For example, a default action may be no action or a specified action. In some cases, a random action selection or rotating member of a defined set of actions may be taken. In some cases, the random action may be selected from a defined set of actions. For example, a random action may be selected such that a large percentage of the time (e.g., up to 80-95% or more) no action is taken when no entry is matched. However, other times the operator may receive a notification to inject variety into the operator's daily/weekly/monthly patterns.

The lookup table may be static or dynamic. Dynamic lookup tables may be updated in response to operator feedback. Feedback may be active or passive. For example, active feedback may include an operator responding to a notification query or sending unsolicited comments or other input to the system. Passive feedback may include the operator responses to a system action, but not expressly tied to the system action by the operator. For example, an operator may stand-up in response to a notification to take a break from sitting. In another scenario, an operator may remain seated in response to the notification to take a break from sitting. An operator passively responding by taking a suggested action may be viewed as positive feedback. An operator passively responding by not taking the suggestion may be viewed a negative feedback or non-feedback. In some cases, passive user feedback may come in the form of moving toward or away from a target. For example, the system may determine a target posture for an operator and adjust one or more OPS actuators in response. If the operator shifts her posture toward the target, the system may determine that the shift is positive feedback. If the operator shifts her posture toward the target posture, the system may determine that the shift is negative feedback.

The system may also dynamically alter the pace of responsive actions based on feedback. In some cases, operators may find rapid changes or notifications to be disruptive. Alternatively, sparsely spaced notification may allow regression and generate no progress toward expressed or implicit goals. Thus, feedback modulated spacing may allow for a balance between progress and operator disruption. For example, the system may take responsive actions while varying the interval of the responsive actions. In an example scenario, the system may increase the interval between responsive actions until feedback, e.g., express or sensor derived, indicates regression from goals. The system may also respond to the change in effectiveness. For example, the system increase the length of the intervals until the fall off in effectiveness accelerates with respect to the amount of increase. In another scenario, the system may decrease the interval until feedback from the operator is received or until gains in effectiveness decelerate with respect to the decrease in interval.

The system may integrate with operator applications. For example, productivity applications may launch automatically based on signature data, building security data, calendar data, occupancy data, or other data. In an example, an email application may be launched when the operator arrives at the office. Additionally or alternatively applications or logons may be terminated when an operator leaves a desk or workstation. Such terminations may reduce surreptitious access of secure data by unauthorized individuals.

The system may also be applied in workplace environments outside offices. In some cases, the system may be applied in environments such as automobiles and heavy machinery. The OPS may utilize cellular or other wireless data connectivity to transfer sensor data to a central analysis system. In an example scenario, an OPS system implemented in a tractor may be used to monitor operator behavior and patterns similar to those described in the office environment, such as sit-down time and or other sedentary patterns. Further, the OPS may also perform environmental monitoring. For example, the OPS may measure and report exposure levels for an operator. For example, expose levels for vibrations, toxins, radiation, or other environmental factors that may have health implications.

The system may also be applied to provide healthcare related notifications for the user. Additionally or alternatively to providing monitoring and warnings for exposure risks, the system may be used for supplying notifications for health related behavioral issues. For example, the system may warn an airline passenger to get up and walk around during a long flight to avoid risk of blood clots. Similarly, warnings about other long periods of sitting may be provided by the system. In some implementations, the system may access health records and supply warnings selectively based on individual operator risk. Additionally or alternatively, warnings may be provided to a health warning filtering system, e.g., maintained by a third party, that will filter the warnings based on individual operator health history. Thus, in some cases, filtering may be applied without sharing health records.

Figure 6:
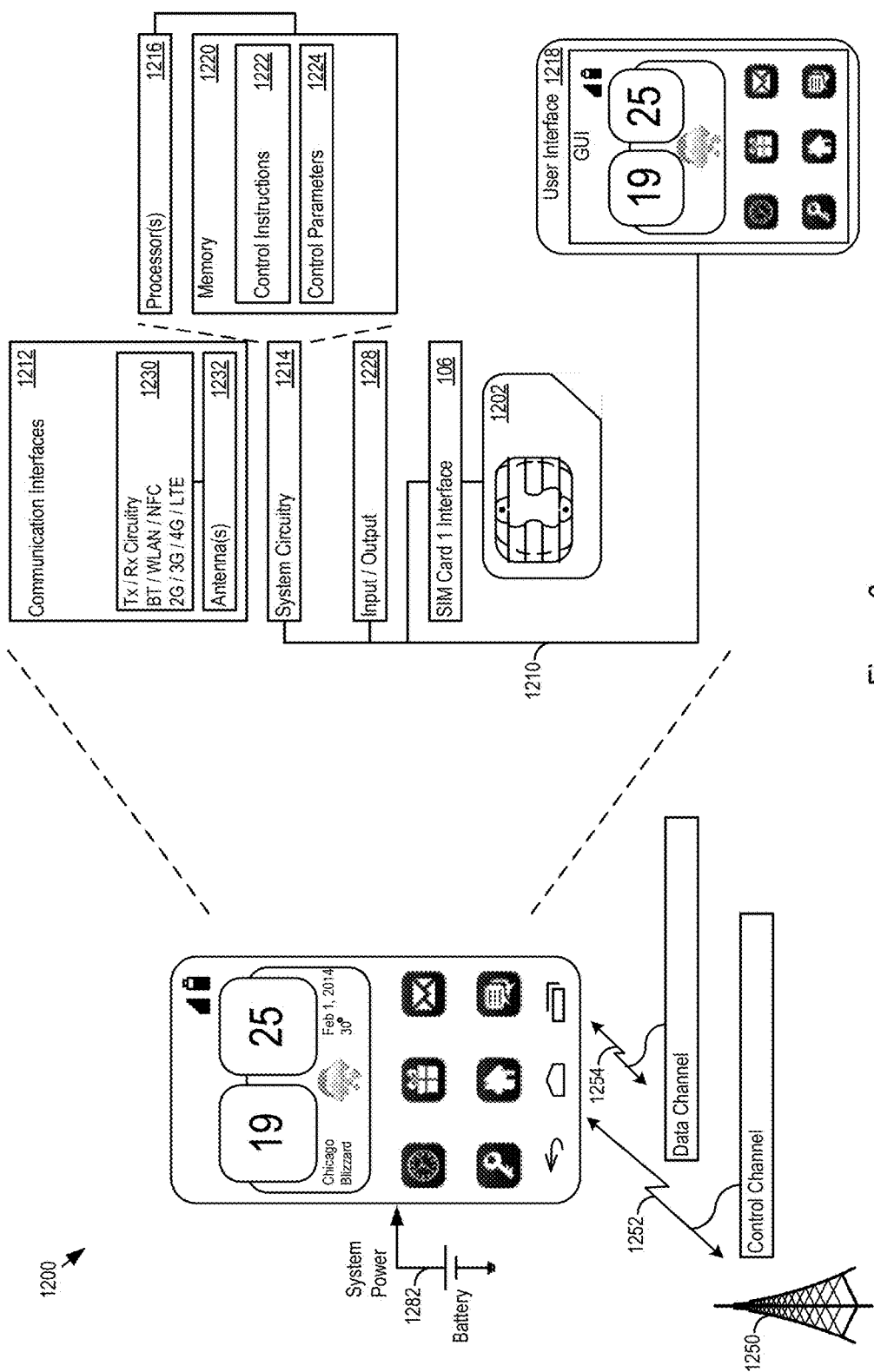
FIG. 6 shows an example mobile device.

The interfaces discussed above may be implemented on operator devices such as mobile device. FIG. 6 show an example mobile device 1200 for interface presentation. The mobile device 1200 is a smartphone in this example, but the mobile device may be any mobile device, such as, but not limited to, a smartphone, smartwatch, smartglasses, tablet, laptop computer, or other device. Accordingly, the smartphone example described below provides just one example context for explaining the architectures and techniques.

As one example, the mobile device 1200 may be a 2G, 3G, 4G/LTE, or faster cellular phone capable of making and receiving wireless phone calls, and transmitting and receiving data using 802.11 a/b/g/n/ac/ad ("WiFi"), Bluetooth (BT), Near Field Communications (NFC), or any other type of wireless technology. The mobile device 1200 may also be a smartphone that, in addition to making and receiving phone calls, runs any number or type of applications.

The example mobile device 1200 may be in communication with a network controller 1250, such as an enhanced Node B (eNB) or other base station. The network controller 1250 and mobile device 1200 establish communication channels such as the control channel 1252 and the data channel 1254, and exchange data. In this example, the mobile device 1200 supports one or more Subscriber Identity Modules (SIMs), such as the SIM 1 1202. Electrical and physical interface 1206 connects SIM 1 1202 to the rest of the user equipment hardware, for example, through the system bus 1210.

The mobile device 1200 includes communication interfaces 1212, system logic 1214, and a user interface 1218. The system logic 1214 may include any combination of hardware, software, firmware, or other logic. The system logic 1214 may be implemented, for example, with one or more systems on a chip (SoC), application specific integrated circuits (ASIC), discrete analog and digital circuits, and other circuitry. The system logic 1214 is part of the implementation of any desired functionality in the mobile device 1200. In that regard, the system logic 1214 may include logic that facilitates, as examples, decoding and playing music and video, e.g., MP3, MP4, MPEG, AVI, FLAC, AC3, or WAV decoding and playback; running applications; accepting user inputs; saving and retrieving application data; establishing, maintaining, and terminating cellular phone calls or data connections for, as one example, Internet connectivity; establishing, maintaining, and terminating wireless network connections, Bluetooth connections, or other connections; and displaying relevant information on the user interface 1218. The user interface 1218 and the inputs 1228 may include a graphical user interface, touch sensitive display, haptic feedback or other haptic output, voice or facial recognition inputs, buttons, switches, speakers and other user interface elements. Additional examples of the inputs 1228 include microphones, video and still image cameras, temperature sensors, vibration sensors, rotation and orientation sensors, headset and microphone input/output jacks, Universal Serial Bus (USB) connectors, memory card slots, radiation sensors (e.g., IR sensors), and other types of inputs.

The system logic 1214 may include one or more processors 1216 and memories 1220. The memory 1220 stores, for example, control instructions 1222 that the processor 1216 executes to carry out desired functionality for the mobile device 1200. The control parameters 1224 provide and specify configuration and operating options for the control instructions 1222. The memory 1220 may also store any BT, WiFi, 3G, or other data 1226 that the mobile device 1200 will send, or has received, through the communication interfaces 1212.

In various implementations, the system power may be supplied by a power storage device, such as a battery 1282

In the communication interfaces 1212, Radio Frequency (RF) transmit (Tx) and receive (Rx) circuitry 1230 handle transmission and reception of signals through one or more antennas 1232. The communication interface 1212 may include one or more transceivers. The transceivers may be wireless transceivers that include modulation/demodulation circuitry, digital to analog converters (DACs), shaping tables, analog to digital converters (ADCs), filters, waveform shapers, filters, pre-amplifiers, power amplifiers and/or other logic for transmitting and receiving through one or more antennas, or (for some devices) through a physical (e.g., wireline) medium.

The transmitted and received signals may adhere to any of a diverse array of formats, protocols, modulations (e.g., QPSK, 16-QAM, 64-QAM, or 256-QAM), frequency channels, bit rates, and encodings. As one specific example, the communication interfaces 1212 may include transceivers that support transmission and reception under the 2G, 3G, BT, WiFi, Universal Mobile Telecommunications System (UMTS), High Speed Packet Access (HSPA)+, and 4G/Long Term Evolution (LTE) standards. The techniques described below, however, are applicable to other wireless communications technologies whether arising from the 3rd Generation Partnership Project (3GPP), GSM Association, 3GPP2, IEEE, or other partnerships or standards bodies.

At other scales of use, such as facilities management, human resources management, and/or other enterprise management, signatures from generalized of aggregated analysis may be used. Further, the sets of signatures used may be tailored to the application of the operator whether the application is enterprise level or individual level. At the enterprise level, the analytics system 200 may provide occupancy tracking, space utilization to performance ratios, aggregate and individual OPS usage information, maintenance feedback, predictive maintenance schedules, aggregate and individual behavior analysis, temperature levels, noise levels, and/or other enterprise data.

Human resources and heath/wellness vendors may also access reports generated by the analytics system 200. These reports may include physical ergonomic reports indicative of physical well-being, cognitive ergonomic reports related to mental health and employee satisfaction for retention purposes, and trend analytics that may be used in interventions and/or other loss prevention activities. These reports may also be used to generate tie-ins to wellness programs or other human resources activities.

In some implementations, job profiles may be determined based on OPS data and other signature data. A human resources department may supply job and task descriptions for various employees. Using the descriptions the system may match the descriptions to collected employee signatures. The collection of signatures may be analyzed to determine job profiles for the supplied job descriptions. The analysis may produce a group of signatures common among employees with a particular description. In some cases, actionable observations may be supplied based on a preformed job profile of an operator prior to determining specific signatures for the operator based on the likely signatures that the operator may have given the operator's job description. For example, OPS types (e.g. seating types, desk types, and/or other OPSs) may be suggested for certain job descriptions. Additionally or alternatively, behavioral actionable observations may be generated based on job description data. For example, action observations about break timing or length may be based on expected periodic tasks or other tasks for a given job description for an operator. Further, posture suggestions may be given as actionable observations. For example, for jobs with long in-seat times, standing breaks may be suggested to an operator that displays a signature of primarily taking seated breaks.

The system may query a human resources database to access job descriptions. Further, the system may send job description updates to the database based on learned behaviors from observation of operators. For example, human resources may provide a given job description that may mismatch behaviors of operators assigned to that description. The analytics system may recognize the mismatch and update the job description.

Additionally or alternatively, OPS maintenance and inventory management may be performed using facility management level data. In an example scenario, an OPS may have an actual age of 7 years, but have usage level similar to an OPS of 12 years. In response to such a determination, action may be taken. For example, the advanced usage OPS may be rotated out for another OPS experiencing unexpectedly light duty. Thus, the overall lifetime of a fleet may be extended. Further, OPSs may be regularly shifted occurring to operator schedules. For example, once a year OPSs may be shifted among known light users and heavy users to result in even wear. In an example, scenario chairs may be exchanged from a 3 shift/week group to a 2 shift/week group to result in even wear. OPSs under recalls or experiencing failures can be pinpointed and replaced or serviced. Further defects can be identified and quickly addressed. In an example scenario, failures may occur in a particular chair brand at a particular age. Chairs of the identified brand and age can be pinpointed and serviced.

The system may be integrated with building functions for heating/cooling control, security functions, lighting control, and/or other functions. For example, an occupant with a foreign signature may be contained in specific non-secure areas. Other security functions such as cameras may enter a secondary mode when a foreign signature is detected. For example, security cameras may record high definition video when a foreign signature is detected. In another example, the definition or frame rate of stored video may be decreased by the system when no occupants are detected. During a drill or emergency situation, the system may be used to determine that occupants have moved to an area of safety or that no occupants are currently in the danger zone. In another scenario, lighting or heating/cooling may be turned off in areas without occupancy.

Vendors may also use management level data to determine product matching for particular clients. For example, if a large portion of users in a particular company sit on the front a chair, it may be beneficial to recommend a chair model that provides support for people perching on the edge of their chairs. Defect identification, as discussed above, may also assist vendors in loss prevention and liability avoidance.

FIGS. 7-10 show example data mappings 610, 620, 630, 640 for various signatures.

Figure 7:
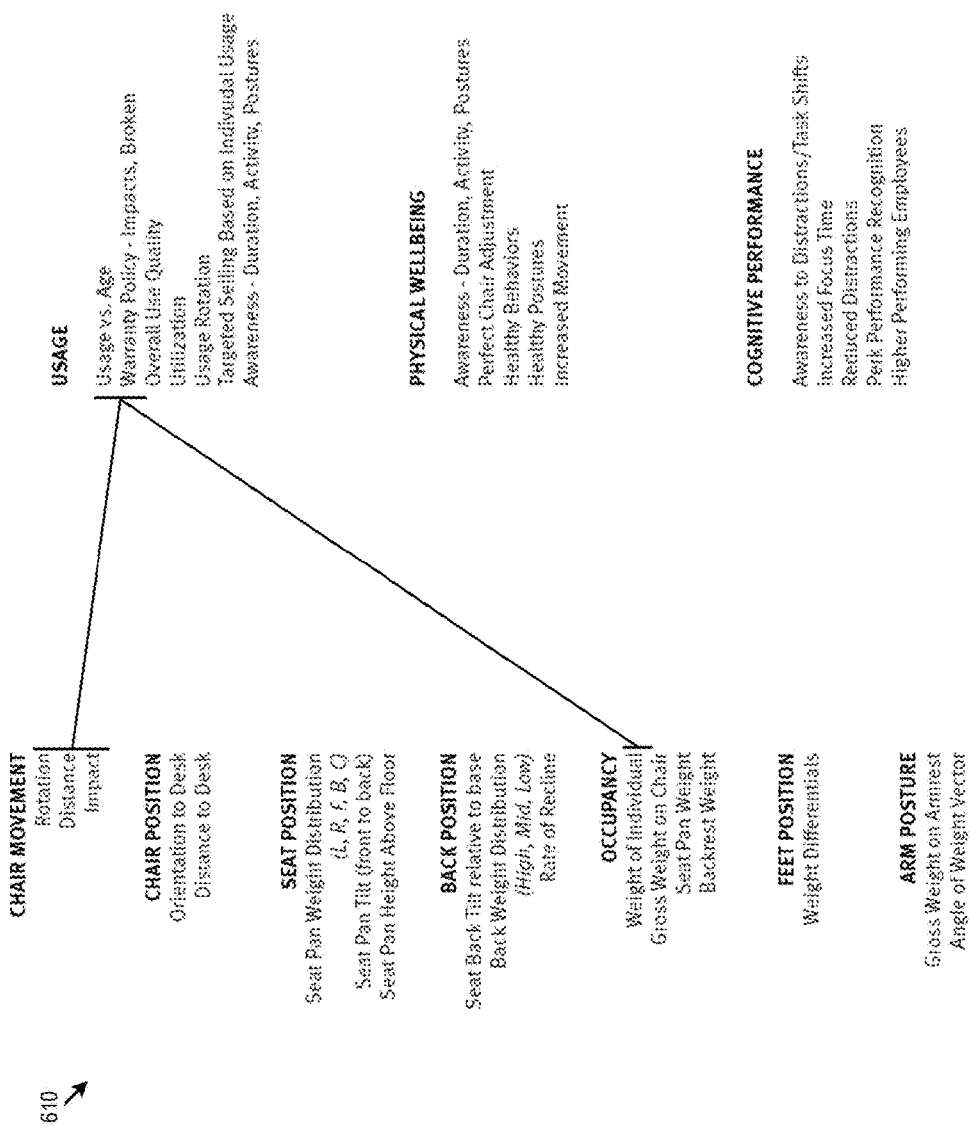
FIG. 7 shows a mapping for determination of usage of a chair and warranty status.

FIG. 7 shows a mapping 610 for determination of usage of a chair and warranty status. Data such as individual weight, chair movement, and/or other data may be processed to determine the usage of a chair and then determine the status of the chair with regard to warrant coverage.

Figure 8:
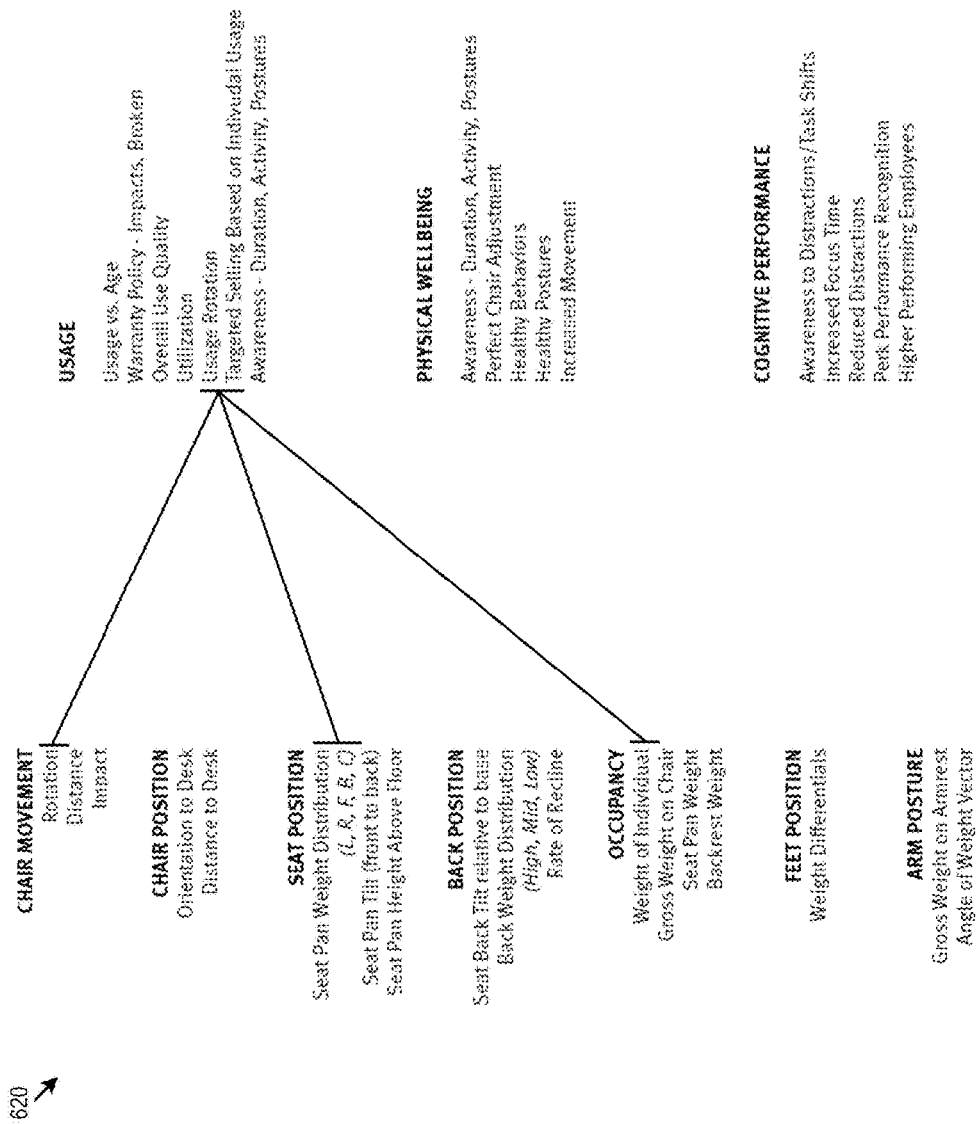
FIG. 8 shows a mapping for determination of rotational usage of a chair and targeted selling.

FIG. 8 shows a mapping 620 for determination of rotational usage of a chair and targeted selling. Data such as seat pan weight distribution, individual weight, chair movement, and/or other data may be processed to determine the rotational usage of a chair and then determine what products may be most suited for the individual operator based on the usage.

Figure 9:
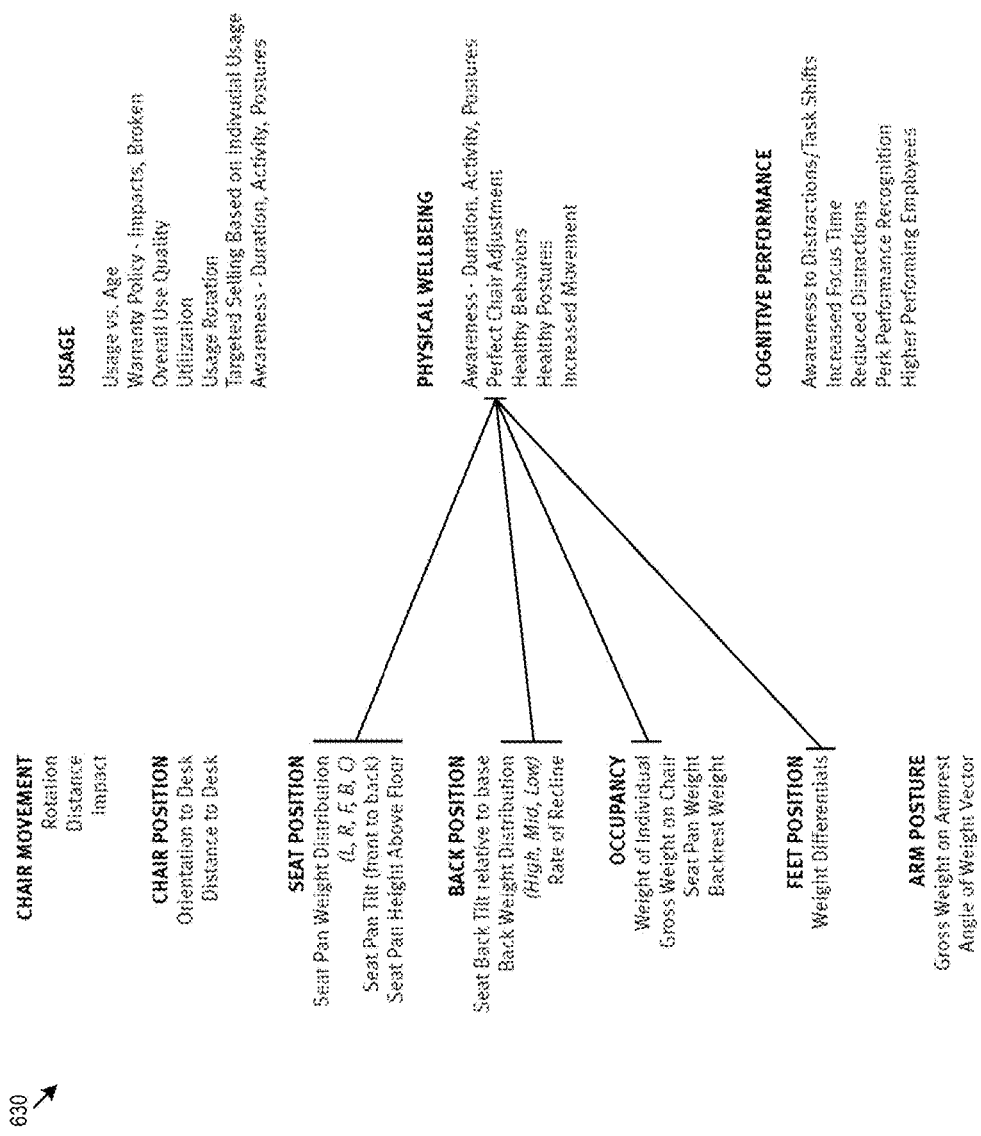
FIG. 9 shows a mapping for determining chair adjustment for an operator.

FIG. 9 shows a mapping 630 for determining chair adjustment for an operator. Data such as seat pan weight distribution, back weight distribution, rate of recline individual weight, and/or other data may be processed to determine adjustments that may lead to improved physical health.

Figure 10:
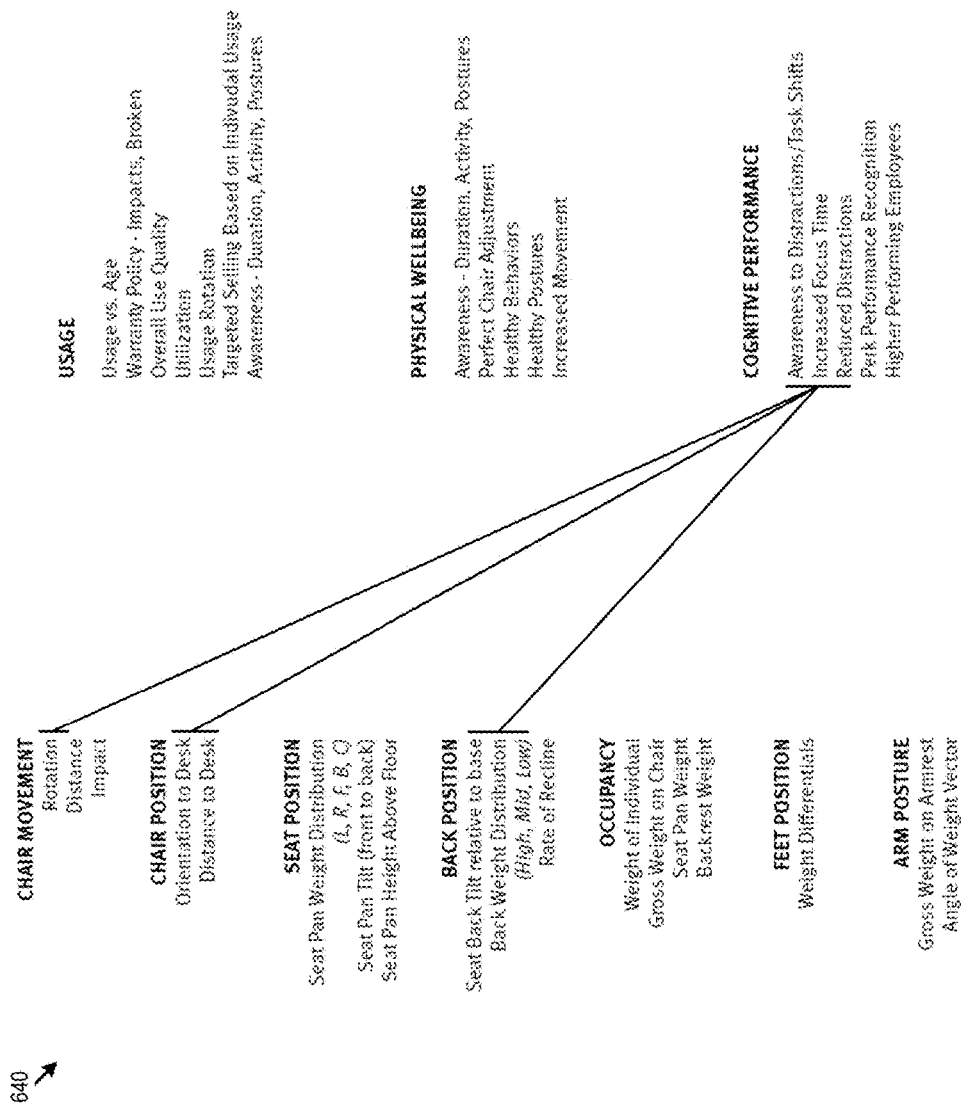
FIG. 10 shows a mapping for focus/distraction analysis for an operator.

FIG. 10 shows a mapping 640 for focus/distraction analysis for an operator. Data such as seat pan weight distribution, back weight distribution, chair orientation and position, chair rotation data, and/or other data may be processed to determine the focus profile for an operator. For example, the system may determine the number of or length of distracted periods versus focused periods. Additionally or alternatively, the system may determine times for suggested breaks based on focus level of an operator. For example a break may be suggested when an operator is distracted. Focus determination may be integrated with other data. For example, accessed calendar data may indicate that the operate has an upcoming meeting. If the operator is distracted from preparation for this meeting, the system may send a reminder to focus on preparation for the upcoming meeting.

Figure 11:
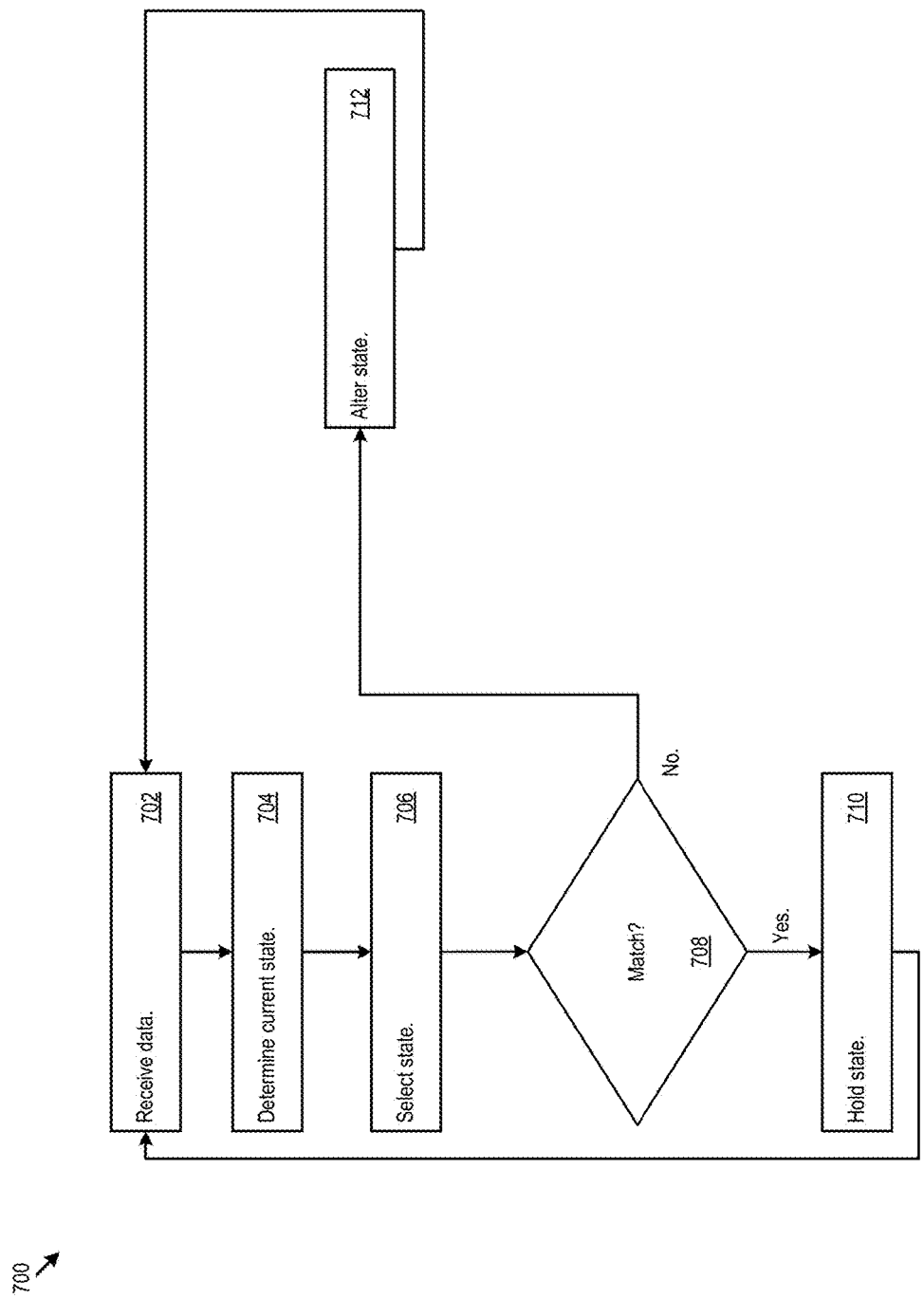
FIG. 11 shows an example enterprise logic.

FIG. 11 shows example enterprise logic 700, which may be executed on the evaluation 422 and contextualization 424 processors. The enterprise logic 700 may receive data (702). For example the enterprise logic 700 may receive data from OPS sensors, applications, building sensors, operator feedback, and/or other data sources. The enterprise logic 700 may determine a current state of one or more enterprise applications (704). The enterprise logic may select a state based on the received data (706). For example, the data may determine that an application should be in a "top visible window" state or active state based on the received data. In another example, the enterprise logic 700 may determine that the state includes sending a push notification that based on the received data. Notifications may include notifications, such as instant messages, text messages, push notification, images, email, sound, video, or other media, based on application data and/or sensor data. For example, a notification may include an actionable observation based on calendar information related to an upcoming meeting and seat-positioning information related to operator focus. The enterprise logic may determine if the current state matches a selected state associated with the received data (708). For example, the system may determine if a selected application is launched or if an appropriate notification is being displayed or was recently displayed. If the current state matches the selected state, the enterprise logic 700 may hold the current state (710) and return to monitoring incoming data (702). If the current state does not match the selected state, the enterprise logic 700 may alter the state of the enterprise application (712) and then return to monitoring incoming data (702).

For example, the notifications may include sending reminders for meetings if the operator is still in her chair as the meeting nears or after it starts. Additionally or alternatively, the enterprise software may ask if an operator needs help, e.g., from a colleague working on the same project, if the operator has been staring at the same PPT or Word page for a time exceeding a determined threshold. Alternatively, the enterprise logic 700 may be used to lock certain applications to prevent operator distraction. For example, if an operator is unusually still or fidgety, the enterprise logic 700 may determine that the operator is distracted. The enterprise logic 700 may lock out certain internet content sources, e.g., sports or video websites, to keep the operator focus on a defined task. Additionally or alternatively, the system may determine distraction based on posture or seat position. In other words, the system 200 may determine that when the user is in certain postures, the user is distracted. The enterprise logic may respond to the identification with a notification encouraging the operator to stay on task. In some cases, operator feedback may be used to identify between actual distractions and productive breaks. For example, an operator may be having a productive, e.g., socially or professionally, discussion with a colleague, which the enterprise logic may flag as a distraction. The enterprise logic 700 may send a notification in response. The operator, after receiving the notification, may reply with feedback indicating that the enterprise logic 700 improperly classified the conversation.

Alternatively or additionally, the enterprise logic 700 may provide notifications about environmental effects. For example, if an operator has been operating machinery with known negative vibration effects and is nearing an exposure limit, the enterprise logic 700 may generate a notification for a dashboard of the device or a mobile device of the operator.

Figure 12:
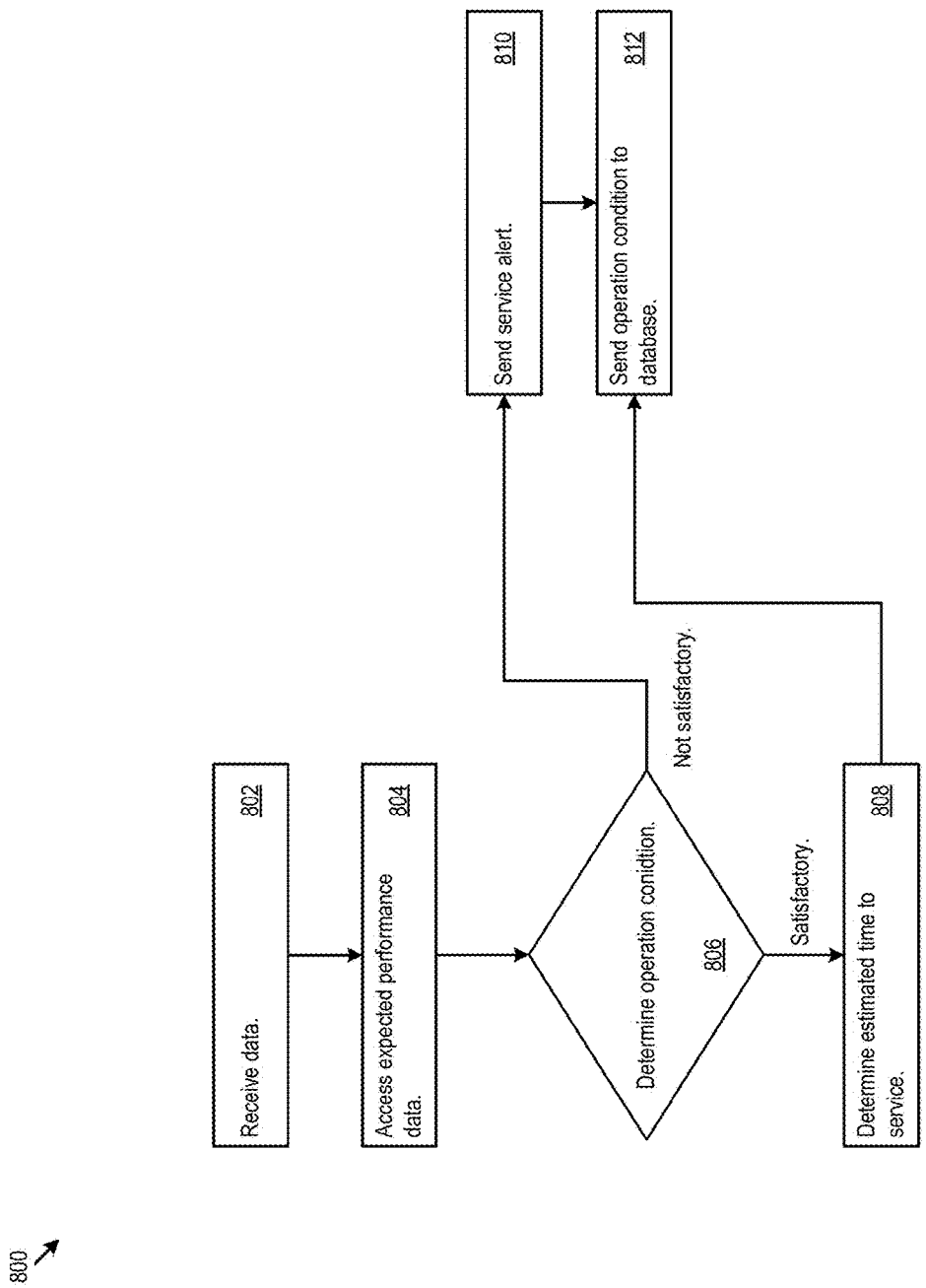
FIG. 12 shows an example maintenance logic.

FIG. 12 shows example maintenance logic 800, which may be executed on the evaluation 422 and contextualization 424 processors. The maintenance logic 800 may receive incoming data from OPSs (802). For example, the incoming data may include usage data, movement data, positioning data, model data, and/or other data. The maintenance logic 800 may access expected performance data for the OPS (804). For example, the maintenance logic 800 may access a supplier database containing lifetime and normal operation parameters for the OPS model. Based on the incoming data and the expected performance data, the maintenance logic 800 may determine an operation condition of the OPS (806). For example, the maintenance logic 800 may determine whether the OPS is operating within a tolerance range defined by the expected performance data. In some cases, the maintenance logic may compare the age of the OPS to the expected lifetime of the OPS. The operation condition may be influenced by one or both of the ratio of age to lifetime and the expected performance data. If the operation condition is determined to be within a satisfactory range, the maintenance logic may determine an estimated time before servicing might be needed based on usage data and the operation condition (808). If the operation condition is outside satisfactory ranges, the maintenance logic may send a service alert (810). For example, the service alert may automatically request a service visit from a technician. In another example, the service alert may be sent to the operator of the OPS to allow the operator determine the appropriate action. The maintenance logic may send the operation condition and selected received data to the database of expected performance data to serve as an additional data point when expected performance is calculated (812). For example, to determine expected performance the maintenance logic 800 may check third party and manufacturer databases for warranty dates, check product recall notices, failure notices, warning notices, recommended use notices or updates, compare against recommended regular preventive service schedules, or perform other maintenance queries.

In some cases, to implement the service alerts the maintenance logic 800 may send messages to service personnel, schedule service visits through automated scheduling systems, check for product upgrades, check to determine if previously ordered parts are ready, keep and update statistics for the OPS manufacturer, or perform other maintenance actions.

Figure 13:
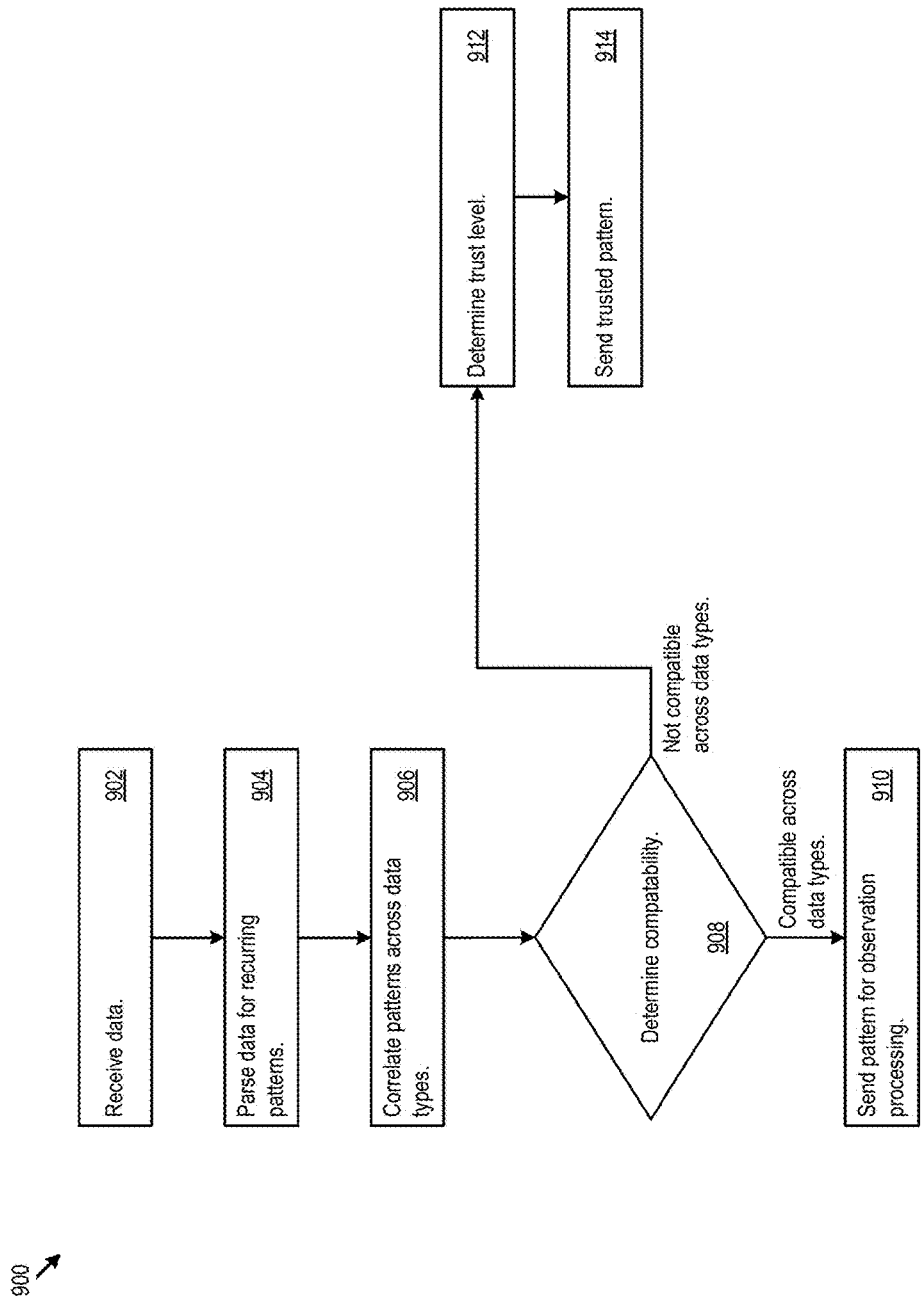
FIG. 13 shows an example occupancy logic.

FIG. 13 shows example occupancy logic 900, which may be executed on the evaluation 422 and contextualization 424 processors. The occupancy logic 900 may receive incoming data from one or more the sources discussed above (902). The occupancy logic 900 may parse the data for recurring patterns (904). For example, the occupancy logic 900 may parse data to determine when occupancy or occupancy groupings, e.g., for an OPS, a room, or other space, may be expected or unexpected. Thus, the occupancy logic may be able to make predictions about future occupancy or space usage. For example, the occupancy logic 900 may determine an unscheduled meeting occurs between certain operators at the same time on repeated weeks. The occupancy logic 900 may recognize this pattern and reserve space for the unscheduled meeting without operator intervention. In some cases, the occupancy logic may add the unscheduled meeting to the operators' calendars, e.g., as a tentatively or firmly scheduled event.

For example, the enterprise logic may perform wavelet analyses to determine periodic patterns. The data may be compared to known states to determine overlap. For example, the occupancy logic 900 may be given a mapping of two or more known application states. The occupancy logic 900 may determine the current state based on a superposition of the two or more known states. Other analyses may be used.

The occupancy logic 900 may correlate patterns across data types (906). For example, calendar data may be compared to seating load sensor data. The occupancy logic may determine if probable patterns derived from a first data set are compatible with patterns derived from other data sets (908). For example, a pattern derived from calendar data may be incompatible with sensor data readings. This may indicate a meeting was cancelled or moved, or that a pattern found was a false positive in either data set. If patterns are found to be consistent across data sets, the occupancy logic 900 may send the pattern to other logic for observation processing (910). If a pattern is found to be inconsistent among data sets, the occupancy logic 900 may determine a level of trust for the pattern (912). For example, a common pattern may have a high level of trust compared to an uncommon pattern. For example, it may be uncommon for an office chair to be occupied when a particular operator is not present. Calendar data may indicate the operator is not present, but the chair load sensor indicates that the chair is occupied. The occupancy logic may determine that the calendar data is incorrect, for example, because schedules may change frequently and operator may not necessarily update calendars. Alternatively, the occupancy logic 900 may determine the chair load sensor is faulty if the sensor has indicated continuous occupancy for an uncommonly long period (e.g., 24 hours or another long period). Alternatively or additionally, anomalous occupancy readings may indicate that an operator has lost consciousness or is otherwise in need of medical assistance. Once a relative level of trust is established, the occupancy logic 900 may send a trusted pattern over other less trusted incompatible patterns (914). The predicted occupancy patterns may be used to alter floor plans to better match expected usage. For example, unused conference space may be converted to sit-down work space or vice versa. In some, cases the conversion may be performed by OPSs with mobility capabilities.

Additionally or alternatively, predicted patterns may be used to control building automation, e.g. HVAC, lighting, security sensors, locks, or other building systems.

Figure 14:
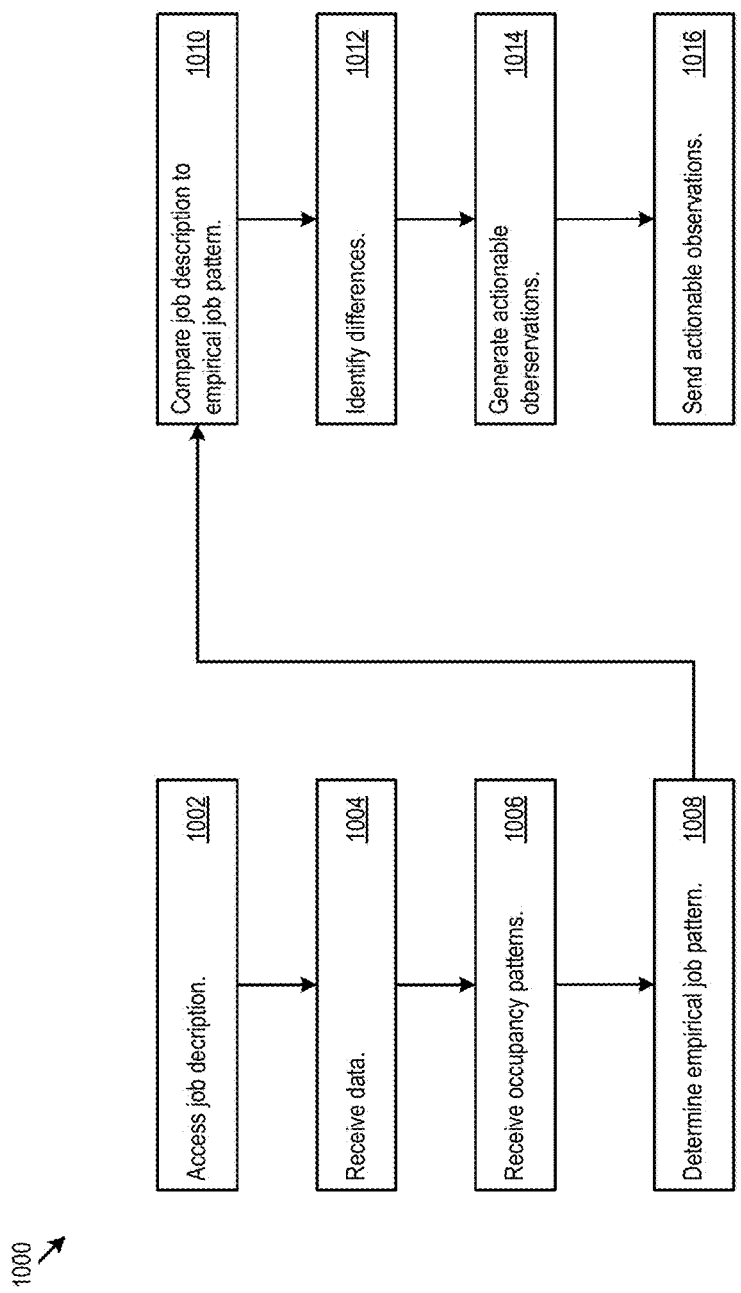
FIG. 14 shows example job logic.

FIG. 14 shows example job logic 1000, which may be executed on the evaluation 422 and contextualization 424 processors. The job logic 1000 may access a job description from a database (1002). For example the job logic 1000 may access job descriptions from a human resources database. The job logic 1000 may receive data incoming data from OPSs (1004). The job logic 1000 may also receive occupancy patterns from occupancy logic 900 (1006). Based on the OPS data and the occupancy patterns, the job logic may determine an empirical job pattern for an operator (1008). The empirical job pattern may include data such as application usage history for the operator, focus profiles, break timings, meeting patterns (e.g., people commonly met with, times commonly used for meetings, and/or other meeting data), posture profiles, and/or other data. The job logic may compare the empirical job pattern to the accessed job description from the database (1010). The job logic 1000 may identify differences between the accessed job description and the empirical job pattern (1012). For example, the system may detect a number of task shifts that is outside an expected range based on the accessed job description. The job logic may generate actionable observations based on the differences (1014). For example, the job logic may indicate that the operator should adjust the operator's average number of daily task shifts to conform with the expected range for the job description. Additionally or alternatively, the job logic 1000 may adjust OPS actuators to set chair height, adjust distance between the operator and monitor, adjust chair back stiffness, limit angle and speed of rotation or other ergonomic adjustment tailored to the job profile. The job logic 1000 may send the actionable observations out for execution (1016). For example, the actionable observations may be sent as push notifications, automated OPS adjustments, application actions, or other actions. For example, using the calendar enterprise application the job logic 1000 may reserve time for practice for jobs requiring skill. In another example, the job logic 1000 may adjust room temperature to assist productivity, e.g., to encourage alertness. In another example, the job logic 1000 may lock applications to limit an operator's distractions or prevent over work. In some cases, the operator may be able to override actions by the job logic 1000. The job logic 1000 may make time usage suggestions based on efficacy rates for other operators with the same job profile.

Figure 15:
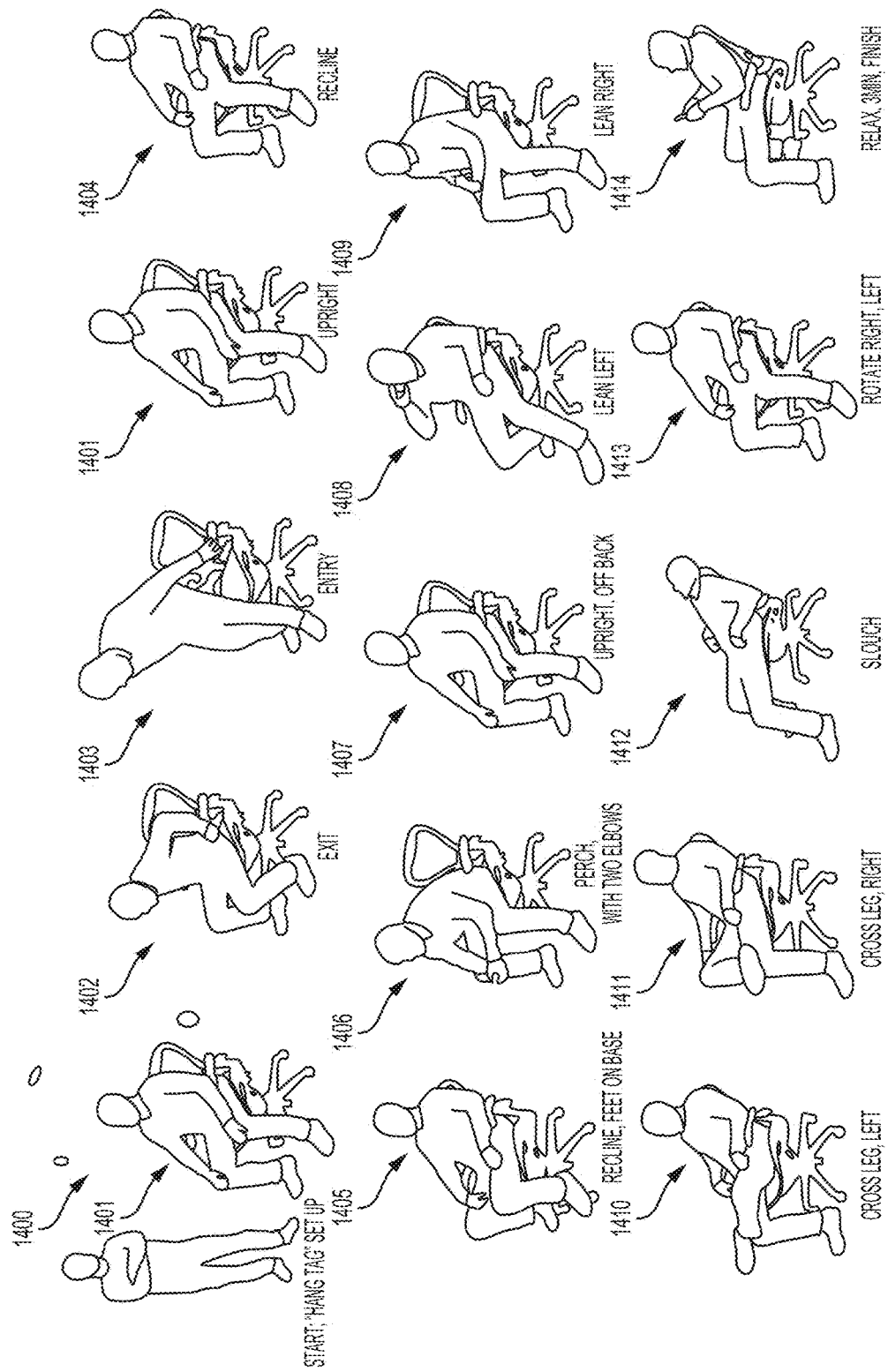
FIG. 15 shows posture logic.

FIG. 15 shows posture logic 1400, which may be executed on the evaluation 422 processor. The posture logic 1400 may receive sensor data such as video data, motion data, pressure data, and/or other data. The posture logic may use the data to classify the posture of the operator into one or more posture states 1401-1414. Once, the posture of the operator is classified. The posture logic 1400 may send the posture state to other logic, e.g., running on the evaluation 422 and contextualization 424 processors, for pattern determination. In some cases, the posture logic may implement an initialization process in which the operator assumes one or more the posture states to allow for later recognition by matching to the initialization states.

The classified posture states may include a upright seated position 1401, a chair exit position 1402, a chair entry position 1403, a chair recline position 1404, a recline position with feet on chair base 1405, a perch position with elbows on knees 1406, an upright and off-backrest position 1407, a lean left position 1408, a lean right position 1409, a cross leg left position 1412, a cross leg right position 1411, a slouch position 1412, a chair rotating state 1413, a relaxed state 1414, and/or other posture states.

The states could be differentiated via different weight distributions on strain sensors in the seat and/or different video or ranging signatures. For example, person leaning to the left may produce extra weight on the left side of the seat pan and/or left armrest. A person sitting upright may have a balanced left/right weight distribution. Similarly, a person in a recline position may produce extra weight on a backrest and have spinal or neck curvature that might be visible via video capture.

The methods, devices, processing, and logic described above may be implemented in many different ways and in many different combinations of hardware and software. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical storage; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

Various implementations have been specifically described. However, many other implementations are also possible. Various features and advantages of the invention are set forth in the following claims.

What is claimed is:

1. A furniture system comprising:
   a chair including
      a seat,
      a backrest coupled to the seat, and
      a base supporting the backrest and the seat;
   a plurality of sensors coupled to the chair, each sensor operable to detect a physical force imparted by a user on the chair, and generate an output signal indicative of the physical force; and
   a processor coupled to the plurality of sensors, and the processor operable to receive the output signals generated by the plurality of sensors,
      determine, based on at least one of the output signals, a current posture of the user sitting in the chair,
      determine, based on at least one of the output signals, a focus profile of the user;
      determine a period of time that the user remains in the current posture,
      generate a notification for the user to change postures when the period of time exceeds a time threshold, and
      generate a notification for the user to change postures when the focus profile of the user indicates the user is distracted.

2. The furniture system of claim 1, wherein the processor is operable to determine, based on the at least one of the output signals, a position parameter of the chair, the position parameter corresponding to a tilt of the seat relative to the base, a distribution of weight on the backrest, or a tilt of the seat relative to a horizontal level, and
   wherein the current posture and the focus profile of the user are determined based on the position parameter.

3. The furniture system of claim 1, wherein the chair further includes a first armrest and a second armrest,
   wherein a first sensor of the plurality of sensors is coupled to the first armrest and operable to determine a first force vector acting on the first armrest, and
   wherein the processor is operable to determine the current posture and the focus profile of the user based on the first force vector.

4. The furniture system of claim 3, wherein a second sensor of the plurality of sensors is coupled to the second armrest and operable to determine a second force vector acting on the second armrest, and wherein the processor is operable to
- determine a difference between the first force vector and the second force vector and
- determine the current posture and the focus profile of the user based on the difference.

5. The furniture system of claim 1, wherein the processor is operable to
- periodically store the current posture of the user,
- generate a report including information regarding stored postures of the user, and transmit the report to a display.

6. The furniture system of claim 5, wherein the report includes a length of time spent in each of the stored postures.

7. The furniture system of claim 5, wherein the report includes information regarding a time spent standing by the user and a time spent sitting by the user, and wherein the time spent sitting is subdivided into the time spent sitting in different postures.

8. The furniture system of claim 1, wherein the processor is operable to
- indicate a target posture to the user, and
- determine, based on the output signals from the plurality of sensors, whether the user moves toward the target posture in response to indicating the target posture to the user.

9. The furniture system of claim 1, wherein the current posture of the user is one selected from a group consisting of: an upright position, a chair recline position, a recline position with feet on the base, a perch position with elbows on knees, and upright and off-backrest position, a lean left position, a lean right position, a cross leg left position, a cross leg right position, and a slouch position.

10. The system of claim 1, wherein the processor is further operable to perform at least one of a group of actions consisting of controlling a furniture piece with mobile capabilities to move, adjusting a height of the chair, adjusting a distance between the user and a monitor, adjusting a back stiffness of the chair, limiting an angle of movement of the chair, and limiting a speed of rotation of the chair.

11. A method of determining a posture of a user sitting in a chair, the chair including a seat, a backrest, and a base, the method comprising:
- detecting, by a plurality of sensors coupled to the chair, a physical force imparted by the user on the chair;
- generating, by each of the plurality of sensors, an output signal indicative of the physical force;
- receiving, by a processor coupled to the plurality of sensors, the output signals generated by the plurality of sensors;
- determining, by the processor, a current posture of the user sitting in the chair based on at least one of the output signals received by the processor;
- determining, by the processor, a focus profile for the user based on the output signals;
- periodically storing, by the processor, the current posture and the focus profile of the user;
- generating, by the processor, a report including information regarding stored postures of the user and the focus profile of the user; and
- transmitting the report to a human resources department to determine at least one ergonomic aspect of the user.

12. The method of claim 11, further comprising:
- determining, by the processor, a position parameter of the chair based on the at least one of the output signals received by the processor, the position parameter corresponding to a tilt of the seat relative to the base, a distribution of weight on the backrest, or a tilt of the seat relative to a horizontal level; and
- wherein determining the current posture of the user includes determining the current posture of the user based on the position parameter; and
- wherein determining the focus profile of the user includes determining the focus profile of the user based on the position parameter.

13. The method of claim 11, wherein the chair further includes a first armrest and a second armrest, and further comprising:
- detecting, by a first sensor of the plurality of sensors coupled to the first armrest, a first force acting on the first armrest; and
- detecting, by a second sensor of the plurality of sensors coupled to the second armrest, a second force acting on the second armrest;
- determining a difference between the first force and the second force; and
- wherein determining the current posture of the user includes determining the current of the user based on the difference first force; and
- wherein determining the focus profile of the user includes determining the focus profile of the user based on the difference first force.

14. The method of claim 13, further comprising:
- detecting, by a second sensor of the plurality of sensors coupled to the second armrest, a second force acting on the second armrest;
- determining a difference between the first force and the second force; and
- wherein determining the current posture of the user includes determining the current posture of the user based on the difference; and
- wherein determining the focus profile of the user includes determining the focus profile of the user based on the difference.

15. The method of claim 11, wherein generating the report includes generating the report including a length of time spent in each of the stored postures.

16. The method of claim 11, further comprising:
- determining, by the processor, a period of time that the user remains in the current position; and
- generating, by the processor, a notification for the user to change postures when the period of time exceeds a time threshold.

17. The method of claim 11, wherein generating the report includes generating the report including information regarding a time spent standing by the user and a time spent sitting by the user; and further comprising subdividing the time spent sitting into the time spent sitting in different postures.

18. The method of claim 11, further comprising:
- indicating, by the processor, a target posture to the user; and
- determining, by the processor and based on the output signals from the plurality of sensors, whether the user moves toward the target posture in response to indicating the target posture to the user.

19. The method of claim 11, wherein determining the current posture of the user includes determining whether the current posture of the user corresponds to one selected from a group consisting of: an upright position, a chair recline position, a recline position with feet on the base, a perch position with elbows on knees, and upright and off-backrest position, a lean left position, a lean right position, a cross leg left position, a cross leg right position, and a slouch position.

20. The method of claim 11, the method further comprising:
- performing, by the processor, at least one of a group of actions consisting of controlling a furniture piece with mobile capabilities to move, adjusting a height of the chair, adjusting a distance between the user and a monitor, adjusting a back stiffness of the chair, limiting an angle of movement of the chair, and limiting a speed of rotation of the chair.

21. A furniture system comprising:
- a chair including
  - a seat,
  - a backrest coupled to the seat, and
  - a base supporting the backrest and the seat;
- a plurality of sensors coupled to the chair, each sensor operable to detect a physical force imparted by a user on the chair, and generate an output signal indicative of the physical force; and
- a processor coupled to the plurality of sensors, and the processor operable to receive the output signals generated by the plurality of sensors,
  - determine, based on at least one of the output signals, a current posture of the user sitting in the chair,
  - compare the current posture to a known user posture signature,
  - determine a period of time that the user remains in the current posture, and
  - generate a notification for the user to change postures when the period of time exceeds a time threshold and the current posture matches the known user posture signature.

* * * * *